US008673581B2

(12) United States Patent
Zeiher et al.

(10) Patent No.: US 8,673,581 B2
(45) Date of Patent: *Mar. 18, 2014

(54) SCD40L AND PLACENTAL GROWTH FACTOR (PLGF) AS BIOCHEMICAL MARKER COMBINATIONS IN CARDIOVASCULAR DISEASES

(75) Inventors: Andreas M. Zeiher, Frankfurt am Main (DE); Christopher Heeschen, Munich (DE); Stefanie Dimmeler, Frankfurt am Main (DE); Christian Hamm, Bad Homburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/613,010

(22) Filed: Sep. 13, 2012

(65) Prior Publication Data

US 2013/0004487 A1  Jan. 3, 2013

Related U.S. Application Data

(63) Continuation of application No. 10/534,985, filed as application No. PCT/EP03/12531 on Nov. 10, 2003, now Pat. No. 8,409,815.

(30) Foreign Application Priority Data

Nov. 16, 2002 (DE) .................................. 102 53 525
Apr. 8, 2003 (DE) .................................. 103 16 059

(51) Int. Cl.
*G01N 31/00* (2006.01)
*G01N 33/53* (2006.01)
(52) U.S. Cl.
USPC ........... 435/7.21; 435/7.1; 436/501; 436/518; 424/130.1; 424/9.1; 530/300; 530/350
(58) Field of Classification Search
None
See application file for complete search history.

(56) References Cited

U.S. PATENT DOCUMENTS

| | | | |
|---|---|---|---|
| 4,477,575 A | 10/1984 | Vogel | |
| 6,333,397 B1 | 12/2001 | Katus | |
| 6,391,311 B1 | 5/2002 | Ferrara et al. | |
| 6,455,283 B1 | 9/2002 | Ferrara et al. | |
| 8,409,815 B2 * | 4/2013 | Zeiher et al. | 435/7.21 |
| 2003/0013134 A1 | 1/2003 | Roth | |
| 2004/0126828 A1 | 7/2004 | Karumanchi et al. | |
| 2006/0008829 A1 | 1/2006 | Hess et al. | |
| 2007/0042438 A1 | 2/2007 | Zeiher et al. | |
| 2009/0155827 A1 | 6/2009 | Zeiher et al. | |
| 2009/0163411 A1 | 6/2009 | Rosendahl et al. | |

FOREIGN PATENT DOCUMENTS

| | | |
|---|---|---|
| CA | 2509063 A1 | 6/2004 |
| EP | 0045476 A1 | 2/1982 |
| EP | 0394819 A2 | 10/1990 |
| EP | 1530047 A1 | 5/2005 |
| EP | 1615036 A1 | 1/2006 |
| JP | 2004-515201 T | 5/2004 |
| JP | 2006-030183 A | 2/2006 |
| WO | WO 92/06194 A1 | 4/1992 |
| WO | WO 98/20155 | 5/1998 |
| WO | WO 98/28006 A1 | 7/1998 |
| WO | WO 99/24056 A1 | 5/1999 |
| WO | WO 99/47677 A2 | 9/1999 |
| WO | WO 01/56593 A2 | 8/2001 |
| WO | WO 01/85796 A2 | 11/2001 |
| WO | WO 02/09683 A2 | 2/2002 |
| WO | WO 02/056015 A1 | 7/2002 |
| WO | WO 02/089730 A2 | 11/2002 |
| WO | WO 03/000183 A2 | 1/2003 |
| WO | WO 03/040691 A2 | 5/2003 |
| WO | WO 03/097688 A2 | 11/2003 |
| WO | WO 2004/046722 A2 | 6/2004 |
| WO | WO 2006/045593 A1 | 5/2006 |

OTHER PUBLICATIONS

Antman et al., "Myocardial infarction redefined—a consensus document of The Joint European Society of Cardiology/American College of Cardiology committee for the redefinition of myocardial infarction," Journal of the American College of Cardiology, vol. 36, pp. 959-969, 2000.
Arboix et al. "Acute Cerebrovascular Disease in Women" Eur. Neurol. 45:199-205 (2001).
Atrial Fibrillation Investigators "Risk Factors for Stroke and Efficacy of Antithrombotic Therapy in Atrial Fibrillation" Arch. Intern. Med. 154:1449-1457(1994).
Aukrust, P. et al., "Enhanced Levels of Soluble and Membrane-Bound CD40 Ligand in Patients With Unstable Angina: Possible Reflection of T Lymphocyte and Platelet Involvement in the Pathogenesis of Acute Coronary Syndromes," Circulation, vol. 100, No. 6, pp. 614-620, (Aug. 10, 1999).
Autiero et al. "Placental growth factor and its receptor, vascular endothelial growth factor receptor-1: novel targets for stimulation of ischemic tissue revascularization and inhibition of angiogenic and inflammatory disorders" J. Thromb. Haemostasis 1:1356-1370 (2003).
Bayes-Genis, A. et al., "Identification of Pregnancy-Associated Plasma Protein A (PAPP-A) as New Marker of Acute Coronary Syndromes," Journal of the American College of Cardiology, vol. 37, No. 2 Supplement A, p. 301 A, XP008028486, (Feb. 2001).

(Continued)

*Primary Examiner* — Lisa Cook
(74) *Attorney, Agent, or Firm* — Finnegan, Henderson, Farabow, Garrett & Dunner, LLP

(57) ABSTRACT

The invention relates to novel markers of vascular inflammation and combinations thereof as diagnostic and prognostic tools in patients with cardiovascular diseases. The markers also act as tools that facilitate the selection of active ingredients for the treatment of such diseases, and finally act as starting points for the treatment of cardiovascular diseases. Furthermore, the invention relates to the creation of an individual risk profile of negative events that are associated with the progression of arteriosclerosis.

22 Claims, 18 Drawing Sheets

(56) References Cited

OTHER PUBLICATIONS

Bayes-Genis, A. et al., "Pregnancy-Associated Plasma Protein A As a Marker of Acute Coronary Syndromes," New England Journal of Medicine, vol. 345, No. 14, pp. 1022-1029, (Oct. 4, 2001).
Belgore et al. "sFlt-1, a Potential Antagonist for Exogenous VEGF" Circulation 102(15):E108-109 (2000).
Belgore et al., "Free and Vascular endothelial growth factor (VEGF) complexed soluble receptor Flt-1 in patients with cardiovascular disease," Journal of the American College of Cardiology, abstract No. 1306-185, vol. 37, No. 2, p. 301A, Feb. 2001.
Belgore et al., "Measurement of free and complexed soluble vascular endothelial growth factor receptor, Flt-1, in fluid samples: development and application of two new immunoassays," Clinical Science, vol. 100, pp. 565-575, 2001.
Biasucci et al., "Clinical use of C-reactive protein for the prognostic stratification of patients with ischemic heart disease," Italian Heart Journal, vol. 2, pp. 164-171, 2001.
Blankenberg et al., "Interleukin-18 is a strong predictor of cardiovascular death in stable and unstable angina," Journal of the American Heart Association, Circulation, vol. 106, pp. 24-30, 2002.
Blann et al. "Vascular endothelial growth factor and its receptor, Flt-1, in the plasma of patients with coronary or peripheral atherosclerosis, or Type II diabetes" Clinical Science 102:187-194 (2002).
Braunwald et al,, ACC/AHA Guideline Update for the Management of Patients With Unstable Angina and Non-ST-Segment Elevation Myocardial Infarction—2002, Journal of the American Heart Association, Circulation, vol. 106, pp. 1893-1900, 2002.
Cao et al. "Placenta Growth Factor: Identification and Characterization of a Novel Isoform Generated by RNA Alternative Splicing" Biochem. Biophys, Res. Commun. 235:493-498(1997).
Carmeliet et at, "Synergism between vascular endothelial growth factor and placental growth factor contributes to angiogenesis and plasma extravasation in pathological conditions," Nature Medicine, vol. 7, pp. 575-583, 2001.
Chung et al. "Angiogenesis in myocardial infarction" Eur. Heart J. 23:1604-1608 (2002).
Chung at al. "Measurement of the soluble angiopoietin receptor tie-2 in patients with coronary artery disease: development and application of an immunoassay" Eur. J. Clin. Invest. 33:529-535 (2003).
Corsini et al., "New Insights Into the Pharmacodynamic and Pharmacokinetic Properties of Statins," Pharmacology Therapeutics, 84: 414-428 (1999).
De Falco, S. et al., "Structure and Function of Placental Growth Factor," Trends in Cardiovascular Medicine, vol. 6, No. 12, pp. 241-246, (2002).
Denktas, A. E. et al., "Pregnancy Associated Plasma Protein-A Levels Are Elevated in Patients With Unstable Angina," European Heart Journal, The European Society of Cardiology, XX, Vo. 23, No. Abstra Suppl, p. 466, XP008028493, (Aug. 31, 2002).
Futterman, L. G. et al., "Novel Markers in the Acute Coronary Syndrome: BNP, IL-6, PAPP-A," American Journal of Critical Care, vol. 11, No. 2, pp. 168-172, (Mar. 2002).
Garlichs, C. D. et al., "Patients with Acute Coronary Syndrome Express Enhanced CD40 Ligand/CD154 on Platelets," Heart, vol. 88, No. 6, pp. 649-655, (Dec. 2001).
Goethe-University Frankfurt am Main "Neuartige Diagnose von Gefäßkrankheiten soll Chancen nach Herzinfarkt verbessern: Dade Behring, Universität Frankfurt and Innovectis unterzeichen exklusives Lizenzabkommen" ("Novel diagnosis of vascular disease after heart attack is to improve opportunities: Dade Behring, University of Frankfurt and Innovectis to sign exclusive licensing agreement") Press Release, Jun. 6, 2005 (German with English translation).
Hajek, P. et al., "Pregnancy-Associated Plasma Protein a (PAPP-a) in Determination of Unstable Coronary Plaque," European Heart Journal, vol. 23, No. Abstract Supplement, p. 293, XP008028492, (2002).
Hauser and Weich "A Heparin-Binding Form of Placenta Growth Factor (PlGF-2) is Expressed in Human Umbilical Vein Endothelial Cells and in Placenta" Growth Factors 9(4):259-268 (1993).

Heeschen et al. "Prognostic Value of Placental Growth Factor in Patients with Acute Chest Pain" JAMA 291(4)435-441 (Jan. 28, 2004).
Heeschen et al., "Serum Level of the Antiinflammatory Cytokine Interleukin-10 is an Important Prognostic Determinant in Patients with Acute Coronary Syndromes," Journal of the American Heart Association, Circulation, vol. 107, pp. 2109-2114, 2003.
Heeschen at al., "Soluble CD40 Ligand in Acute Coronary Syndromes," The New England Journal of Medicine, vol. 348, No. 12, pp. 1104-1111, 2003.
Heeschen et at, "Placental Growth Factor: A Novel Serum Marker of Vascular Inflammation . . . the Risk of Patients with Acute Coronary Syndromes," Journal of the American Heart Association, Supplement to Circulation, abstract No. 2152, vol. 108, No. 17, Oct. 28, 2003.
Heeschen etal. "Plasma Levels of the Soluble fms-like Tyrosine Kinase 1 (VEGF receptor 1) Modulate the Prognostic Impact of Placental Growth Factor in Patients Post Myocardial Infarction" Circulation 110(17 Suppl.):III-411, Abstract 1942 (Oct. 26, 2004).
Heeschen, C. et al., "CD40 Ligand Serum Levels Independently Predicts Outcome and Effect of Anti-Platelet Therapy in Patients with Unstable Angina," Circulation, vol. 106, No. 19 Supplement, p. II. 402, XP008028499, (Nov. 5, 2002).
Iyer, S. et al., "Role of Placenta Growth Factor in Cardiovascular Health," Trends in Cardiovascular Medicine, vol. 12, No. 3, pp. 128-134, (2002).
Japanese Patent Application No. 2007-537233: Notification of Reasons for Refusal; Dispatch Date: Aug. 3, 2010 (English translation).
Japanese Patent Application No. 2008-510477: Notice of Reasons for Rejection; Mailing Date: Jan. 10, 2012.
Khosravi, J. et al., "Pregnancy Associated Plasma Protein-A: Ultrasensitive Immunoassay and Determination in Coronary Heart Disease," Clinical Biochemistry, vol. 35, No. 7, pp. 531-538, (2002).
Lenderlink et al., "Elevated troponin T and C-reactive protein predict impaired outcome for 4 years in patients with refractory unstable angina, and troponin T predicts benefit of treatment with abciximab in combination with PTCA," European Heart Journal, vol. 24, pp. 77-85, 2003.
Libby et al., "Inflammation and Atherosclerosis," Journal of the American Heart Association, Circulation, vol. 105, pp. 1135-1143, 2002.
Lindahl et al., "Markers of myocardial damage and inflammation in relation to long-term mortality in unstable coronary artery disease," The New England Journal of Medicine, vol. 343, No. 16, pp. 1139-1147, 2000.
Lund et al., "Circulating Pregnancy-Associated Plasma Protein A Predicts Outcome in Patients with Acute Coronary Syndrome but No Troponin I Elevation," Journal of the American Heart Association, Circulation, vol. 108, pp. 1924-1926, 2003.
Luttun et al., "Placental Growth Factor (PlGF) and Its Receptor Flt-1 (VEGFR-1)," Ann. NY. Acad. Sci., vol. 979, pp. 80-93, 2002.
Luttun, A. et al., "Revascularization of Ischemic Tissues by PlGF Treatment, and Inhibition of Tumor angiogenesis, Arthritis and Atherosclerosis by Anti-Flt1," Nature Medicine. vol. 8, No. 8, pp. 831-840, (Aug. 2002).
Maglione et al. "Isolation of a human placenta cDNA coding for a protein related to the vascular permeability factor" Proc. Natl Acad. Sci USA 88:9267-9271 (1991).
Maglione, D. et al., "Recombinant Production of PlGF-1 and Its Activity in Animal Models," Il Farmaco, vol. 55, pp. 165-167, (2000).
Maynard et al. "Excess placental soluble fms-like tyrosine kinase 1 (sFlt1) may contribute to endothelial dysfunction, hypertension, and proteinuria in preeclampsia" J. Clin. Invest. 111:649-658 (2003).
Novo et al. "Soluble CD40L and Cardiovascular Risk in Asymptomatic Low-Grade Carotid Stenosis," Stroke, American Heart Association, 36:673-675 (2005).
Official Action in German Patent Application No. 102 53 525,6-52 (Feb. 10, 2003).
Onoue et al. "Plasma Level of Soluble Fms-like Tyrosine Kinase 1 (sFlt-1) as a Predictive Maker of Acute Severe Heart Failure in Patients with Acute Myocardial Infarction" Circulation 116(16 Supplement II):II-578, Abstract 2610 (Oct. 16, 2007).

(56) References Cited

OTHER PUBLICATIONS

Peng, D. Q. et al., "Elevated Soluble CD40 Ligand is Related to the Endothelial Adhesion Molecules in Patients with Acute Coronary Syndrome," Clinica Chimica Acta, vol. 319, No. 1, pp. 19-26, (May 7, 2002).

Ridker et al., "C-Reactive Protein, the Metabolic Syndrome, and Risk of Incident Cardiovascular Events: An 8-Year follow up of 14 719 Initially Healthy American Women," Journal of the American Heart Association, Circulation, vol. 107, pp. 391-397, 2003.

Roger et al. "Sustained Hemodynamic Effects of an Infusion of Nesiritide (Human b-Type Natriuretic Peptide) in Heart Failure" J. Am. Coll. Cardiol. 34(1):155-162 (1999).

Scheufler et al. "Implications of Vascular Endothelial Growth Factor, sFlt-1, and sTie-2 in Plasma, Serum and Cerebrospinal Fluid During Cerebral Ischemia in Man" J. Cerebral Blood Flow & Metab. 23:99-110 (2003).

Schönbeck, U. et al., "Soluble CD40L and Cardiovascular Risk in Women," Circulation, vol. 104, No. 19, pp. 2266-2268, (Nov. 6, 2001).

Smith et al. "AHA/ACC Guidelines for Preventing Heart Attack and Death in Patients with Atherosclerotic Cardiovascular Disease: 2001 Update" Circulation 104:1577-1579 (2001).

Torry et al. "Preeclampsia is associated with reduced serum levels of placental growth factor" Am. J. Obstet. Gynecol. 179:1539-1544 (1998).

U.S. Appl. No. 11/666,164, filed Nov. 12, 2008, by Zeiher et al.: Office Action dated Dec. 27, 2010.

U.S. Appl. No. 11/666,164, filed Nov. 12, 2008, by Zeiher et al.: Office Action dated May 19, 2011.

U.S. Appl. No. 11/666,164, filed Nov. 12, 2008, by Zeiher et al.: Examiner Interview Summary dated Jun. 7, 2011.

U.S. Appl. No. 11/666,164, filed Nov. 12, 2008, by Zeiher et al.: Office Action dated Jan. 26, 2012.

Varo, N. et al., "Soluble CD40L: Risk Prediction After Acute Coronary Syndromes," Circulation, vol. 108, No. 9, pp. 1049-1052, (Sep. 2, 2003).

Vuorela-Vepsalainen, P. et al., "Vascular Endothelial Growth Factor is Bound in Amniotic Fluid and Maternal Serum," Human Reproduction, vol. 14, No. 5, pp. 1346-1351, (1998).

Weber et al. "Prognostic Value of the Soluble PLGF Receptor sFlt-1 in Patients Presenting with an Acute Coronary Syndrome" Circulation 116(16 Supplement II):II-578, Abstract 2611 (Oct. 16, 2007).

Weber et al. "Prognostische Bedeutung des löslichen PlGF Rezeptors sFlt-1 bei Patienten mit akuten Koronarsyndromen" ("Prognostic Significance of the Soluble PlGF Receptor SFlt-1 in Patients with Acute Coronary Syndrome") Clin. Res. Cardiol. 96(Suppl. 1):Abstract V1913 (2007) (German).

Yan, J. et al., "Clinical Implications of Increased Expression of CD40L in Patients with Acute Coronary Syndromes," Chinese Medical Journal, vol. 115, No. 4, pp. 491-493, (Apr. 2002).

* cited by examiner

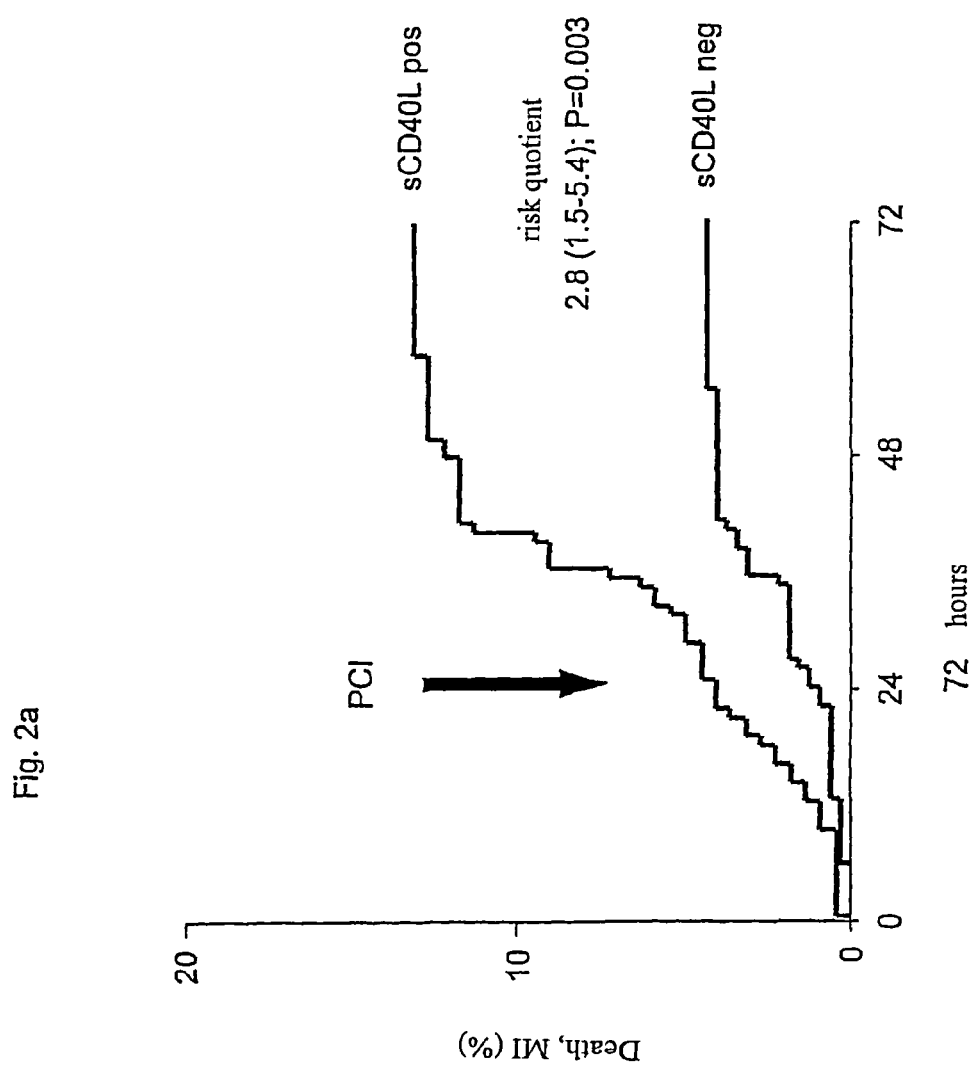

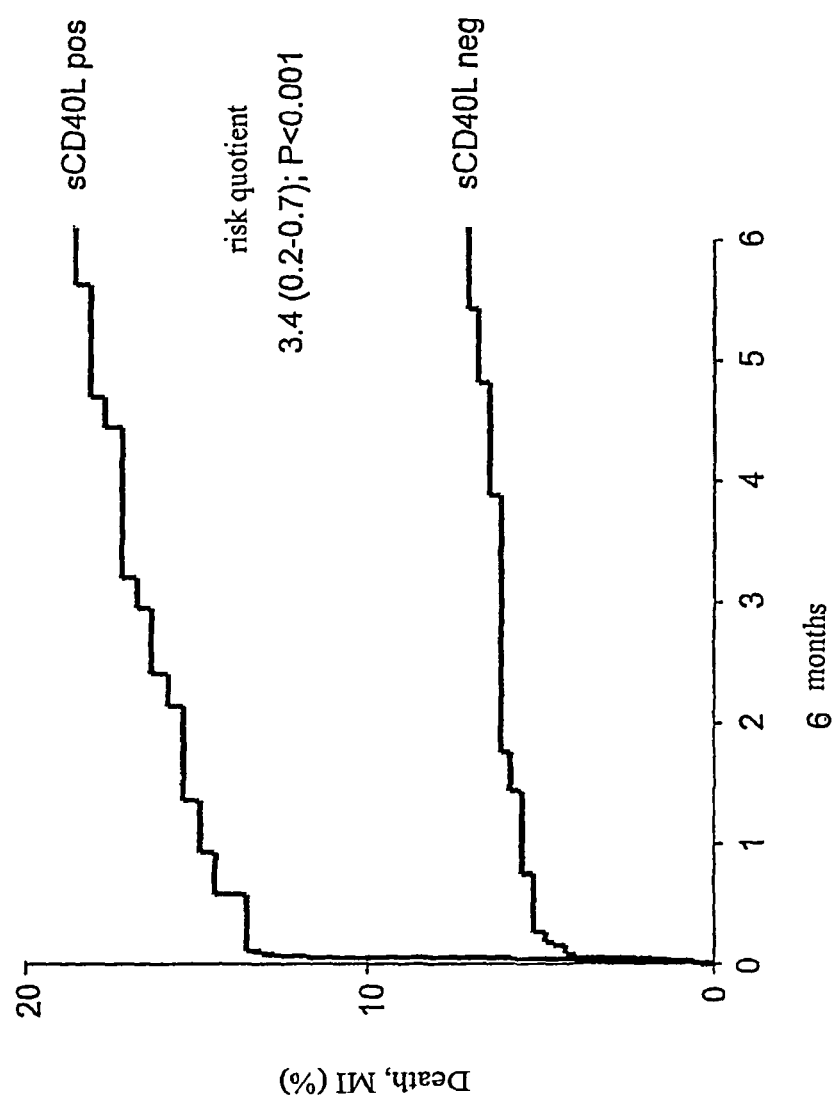

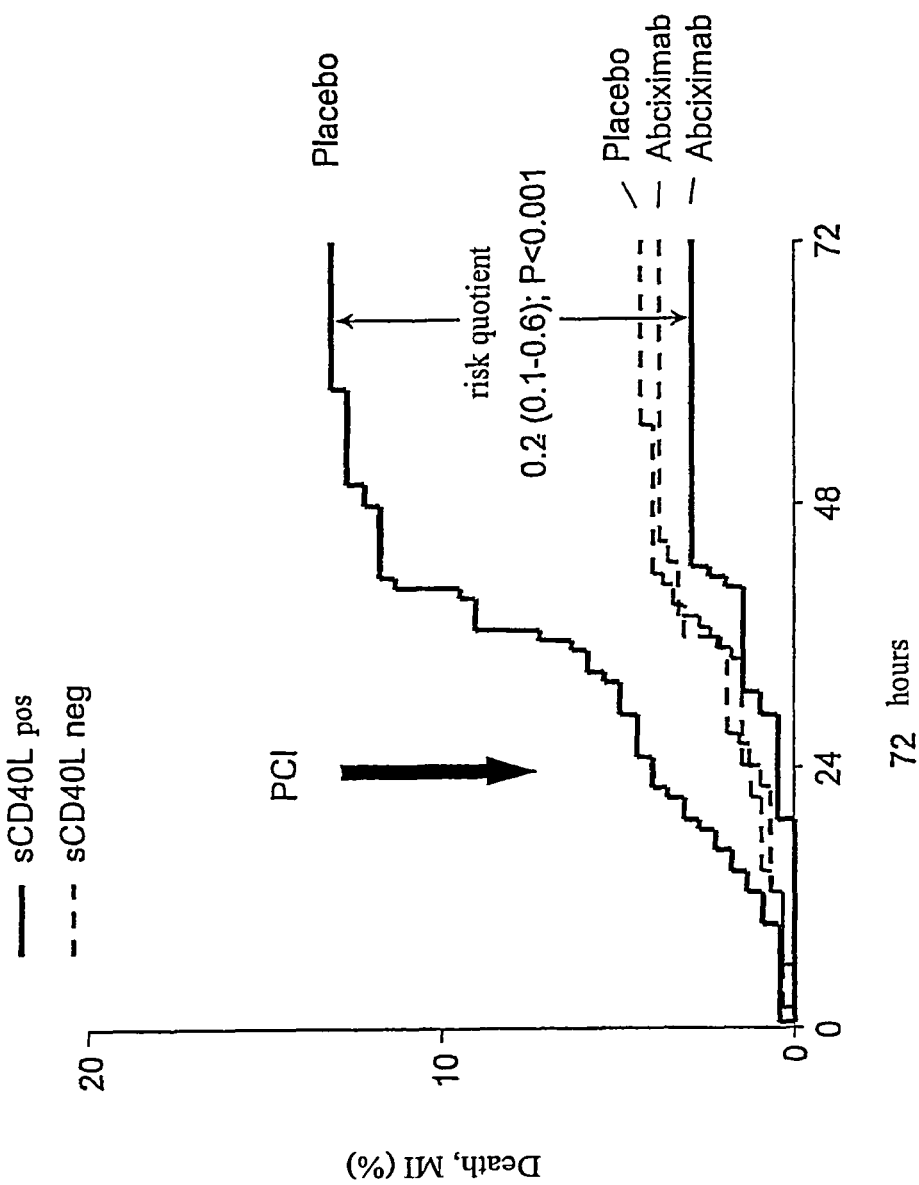

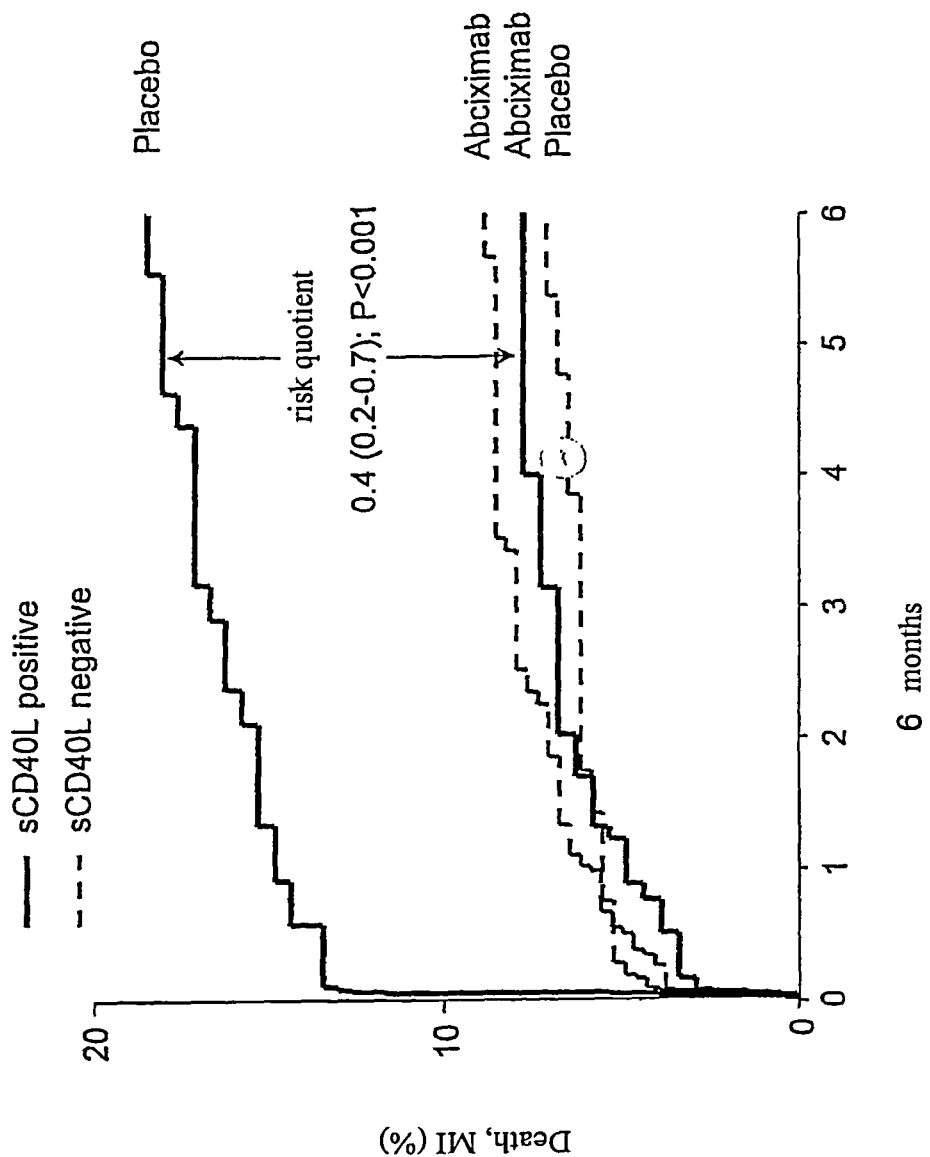

*p < 0,001 versus PlGF low

*p < 0,01 versus PlGF low

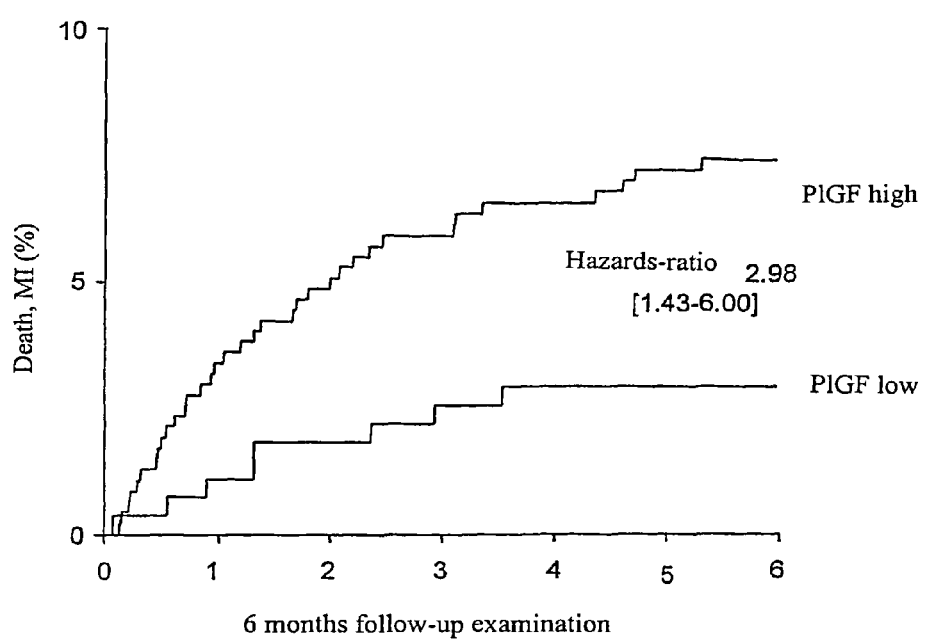

* P<0.01 versus PAPP-A low

* P<0.001 versus PAPP-A low

* P<0.05 versus PAPP-A low

SCD40L AND PLACENTAL GROWTH FACTOR (PLGF) AS BIOCHEMICAL MARKER COMBINATIONS IN CARDIOVASCULAR DISEASES

This application is a continuation of application Ser. No. 10/534,985, which was filed May 16, 2005, and issued as U.S. Pat. No. 8,409,815 which is a National Stage Entry under 35 USC §371 of International Application Number PCT/EP03/12531, filed on Nov. 10, 2003, which claimed priority under 35 USC §119 to German Application No. 102 53 525.6, filed on Nov. 16, 2002, and to German Application No. 103 16 059.0, filed on Apr. 8, 2003, all of which are incorporated by reference in their entirety.

The invention relates to novel markers of vascular inflammation and combinations thereof as diagnostic and prognostic tools in patients with cardiovascular diseases. The markers also act as tools that facilitate the selection of active ingredients for the treatment of such diseases, and finally act as starting points for the treatment of cardiovascular diseases. Furthermore, the invention relates to the creation of an individual risk profile of negative events that are associated with the progression of arteriosclerosis.

BACKGROUND OF THE INVENTION

The formation of a thrombus in the coronary vessel is the triggering event of an unstable coronary heart disease. In patients with an unstable coronary heart disease, the central role of the activation of platelets is further enhanced by thromboxane and prostaglandin metabolites that are released from the platelets. Thus, the activation of platelets is a general therapeutic goal. Until now, such therapies comprised the use of aspirin, tienopyridines and a direct glycoprotein IIb/IIIa-inhibitor. Nevertheless, until today, a reliable biochemical marker for the activation of platelets could not be identified. Results with P-selectin, the yet most promising marker for an activation of platelets, until today, are controversial.

Individuals that suffer from a cardiovascular disease can be grouped into individuals that do not exhibit symptoms, and those that exhibit chest pain. The latter group can be grouped into individuals that exhibit a stable angina pectoris (SAP), and those with acute coronary syndromes (ACS). ACS patients can exhibit an unstable angina pectoris (UAP), or these patients already suffered from a myocardial infarction (MI). The MI can be an ST-elevated MI or a non ST-elevated MI. The occurrence of an MI can be associated by a left ventricular dysfunction (LVD). Finally, LVD patients experience a congestive heart failure (CHF) with a mortality rate of about 15%, or do not exhibit any symptoms.

Patients that are admitted with chest pain are analysed for an ST increase or depression. If this is the case, the individual will remain in hospital with a probability of nearly 100%. Since not all individuals with an MI exhibit ST-abnormalities, the troponin (TnT) level is determined, which in case of extraordinary high values indicates a high probability that an MI has occurred.

Recent progresses in the basic research have established a fundamental role for the inflammation in the mediation of all phases of the arteriosclerosis, from its beginning through progression, and, finally, to the thrombotic complications of arteriosclerotic lesions [Libby P, Ridker P M, Maseri A. Inflammation and atherosclerosis. Circulation 2002; 105(9): 1135-43. Ross R. Atherosclerosis—an inflammatory disease. N Engl J Med 1999; 340(2):115-26. Davies M J, Thomas A C. Plaque fissuring—the cause of acute myocardial infarction, sudden ischemic death, and crescendo angina. Br Heart J 1985; 53(4):363-73. Libby P. Molecular bases of the acute coronary syndromes. Circulation 1995; 91(11):2844-50]. The results obtained from the association between inflammation and arteriosclerosis form the rational for the use of circulating inflammatory markers as potential predictive instruments in patients with acute coronary syndromes. Indeed, elevated levels of inflammatory markers, such as, for example, high sensitive C-reactive protein (hsCRP), serum amyloid A, and interleukin-6 (IL-6) are not only associated with acute coronary syndromes in general [Berk B C, Weintraub W S, Alexander R W. Elevation of C-reactive protein in "active" coronary artery disease. Am J Cordial 1990; 65(3): 168-72, Biasucci L M, Vitelli A, Liuzzo G, et al. Elevated levels of interleukin-6 in unstable angina. Circulation 1996; 94(5):874-7], but—what is more important—can also predict a statement regarding the clinical outcome of patients with acute coronary syndromes [Liuzzo G, Biasucci L M, Gallimore J R, et al. The prognostic value of C-reactive protein and serum amyloid a protein in severe unstable angina. N Engl J Med 1994; 331(7):417-24, Biasucci L M, Liuzzo G, Grillo R L, et al. Elevated levels of C-reactive protein at discharge in patients with unstable angina predict recurrent instability. Circulation 1999; 99(7):855-60, Toss H, Lindahl B, Siegbahn A, Wallentin L. Prognostic influence of increased fibrinogen and C-reactive protein levels in unstable coronary artery disease. FRISC Study Group. Fragmin during Instability in Coronary Artery Disease. Circulation 1997; 96(12):4204-10.]. Although the "classical" acute phase protein hsCRP is regarded as the most promising biomarker for clinical uses, a substantial heterogeneity exists regarding the prevalence of elevated hsCRP levels in patients with acute coronary syndromes [Biasucci L M, Liuzzo G, Colizzi C, Rizzello V. Clinical use of C-reactive protein for the prognostic stratification of patients with ischemic heart disease. Ital Heart J 2001; 2 (3): 164-71.].

Thus, more than 30% of the patients with severe unstable angina do not exhibit elevated hsCRP levels [Liuzzo G, Biasucci L M, Gallimore J R, et al. The prognostic value of C-reactive protein and serum amyloid a protein in severe unstable angina. N Engl J Med 1994; 331(7): 417-24, Heeschen C, Hamm C W, Bruemmer J, Simeons M L. Predictive value of C-reactive protein and troponin T in patients with unstable angina: a comparative analysis. CAPTURE Investigators. Chimeric c7E3 Anti-Platelet Therapy in unstable angina refractory to standard treatment trial. J Am Coll Cardiol 2000; 35(6): 1535-42.]. In addition, individual differences in the extent of the response to certain inflammatory stimuli possibly can affect the levels of the "downstream" acute-phase reactants, such as hsCRP [Pepys M B, Hirschfield G M. C-reactive protein and its role in the pathogenesis of myocardial infarction. Ital Heart J 2001, 2(11): 804-6, Liuzzo G, Biasucci L M, Rebuzzi A G, et al. plasma protein acute-phase response in unstable angina is not induced by ischemic injury. Circulation 1996; 94(10): 2373-80.]. Therefore, still an important challenge exists to identify proximal stimuli for vascular inflammation that can be used as risk-predicting serum markers in patients with coronary arteriosclerosis.

In the meantime, there is increasing evidence that the CD40-CD40L-system plays an important role in the pathophysiology of patients with unstable coronary heart disease. Apart from the cell-associated form, CD40L also occurs in a soluble biologically completely active form, namely sCD40L. sCD40L is shedded by stimulated lymphocytes and actively released upon platelet stimulation. sCD40L acts pro-inflammatory on endothelial cells and promotes the coagulation, in that monocytes and endothelial cells are stimulated to express tissue factors. In addition, sCD40L contains a KGD-sequence, a known binding motif that is specific for the predominant platelet-integrin αIIbβ3. CD40L indeed is a αIIβ3-ligand, a platelet agonist, and is required for the stability of arterial thrombi. An increase of sCD40L can be detected in serum of patients with acute coronary syndromes. It was reported (Schonbeck U, Varo N, Libby P, Buring J, Ridker P M. Circulation 2001; 104: 2266-8) that apparently healthy women which exhibited elevated plasma concentrations of sCD40L, at the same time, carried an increased risk for cardiovascular events.

New findings show that a rupture of plaques and the subsequent formation of a thrombus in patients with acute coronary syndromes can lead to an activation of the exposure of CD40L in circulating platelets (Lee Y, Lee W H, Lee S C, Ahn K J, Choi Y H, Park S W, Seo J D, Park J E. Cardiology. 1999; 92: 11-6). In addition, increased concentrations of sCD40L were detected in patients with angina, whereby the concentrations were particularly high in patients with unstable angina (Aukrust P, Muller F, Ueland T, Berget T, Aaser E, Brunsvig A, Solum N O, Forfang K, Froland S S, Gullestad L. Circulation 1999; 10: 614-20). These results suggest that a CD40L-CD40-interaction plays an important role during the pathogenesis of arteriosclerotic processes and the development of coronary syndromes.

Establishing the correct diagnosis associated with a suitable treatment of patients with acute coronary syndromes that are not associated with an elevation of the ST-stretch can be very cumbersome. The exclusion of acute myocardial infarction in accordance with actual standards is unsatisfactory. In the last years, a focussing on the risk stratification and control of the treatment has occurred with the aim to identify patients wherein the risk exists to develop a life-threatening cardiologic event, and which, in particular, benefit from improved therapeutic and intervening strategies (Hamm C W, Bertrand M, Braunwald E. Lancet 2001; 358:1533-8). In this respect, the ECG has only limited prognostic relevance since important abnormalities are rare and their detection is sparsely sensitive and specific (Kaul P, Fu Y, Chang W C, et al., J Am Coll Cardiol 2001; 38:64-71, and Savonitto S, Ardissino D, Granger C B, et al. JAMA 1999; 281: 707-13). Thus, markers of a necrosis of myocardial cells, in particular cardiac troponines, have developed into valuable tools in the evaluation of patients with acute coronary syndromes (Hamm C W, Braunwald E. Circulation 2000; 102: 118-22). Nevertheless, troponines are not actively involved in the pathophysiology of acute coronary syndromes, but rather represent a kind of surrogate markers for the fragile thrombus formation (Lindahl B, Diderholm E, Lagerqvist B, Venge P, Wallentin L. J Am Coll Cardio. 2001; 38: 979-86, Heeschen C, van Den Brand M J, Hamm C W, Simoons M L. Circulation 1999; 100: 1509-14; Benamer H, Steg P G, Benessiano J, et al. Am Heart J 1999; 137: 815-20). In this respect, the ECG has only limited prognostic relevance since important abnormalities are rare and their detection is sparsely sensitive and specific (Kaul P, Fu Y, Chang W C, et al., J Am Coll Cardiol 2001; 38:64-71 and Savonitto S, Ardissino D, Granger C B, et al. JAMA 1999; 281:707-13).

Markers of an activation of platelets that determine the activity of the disease, preferably before a myocardial necrosis occurs, could represent important additional information for the diagnostic and therapeutic stratification in patients with acute coronary syndromes. There is increasing evidence that also the CD40-ligand (CD40L, recently renamed into CD154) plays an important role in the development of the disease and plaque-destabilisation (Mach F, Schonbeck U, Sukhova G K, Atkinson E, Libby P. Nature 1998; 394: 200-3 and Lutgens E, Gorelik L, Daemen M J, et al. Nat Med 1999; 5: 1313-6). The CD40-CD40L-system is common in a multitude of leukocytes and non-leukocytic cells, including endothelial cells and smooth muscle cells (Schonbeck U, Libby P. Cell Mol Life Sci 2001; 58: 4-43), as well as in activated platelets (Henn V, Slupsky J R, Grafe M, et al. Nature 1998; 391: 591-4). In addition to the cell-associated 39-kDa form, CD40L also occurs in a soluble biologically completely active form, namely sCD40L (Graf D, Muller S, Korthauer U, van Kooten C, Weise C, Kroczek R A. Eur J Immunol 1995; 25: 1749-54). sCD40L is shedded by stimulated lymphocytes and is actively released upon activation of platelets (Lee Y, Lee W H, Lee S C, et al. Cardiology 1999; 92: 11-6, and Henn V, Steinbach S, Buchner K, Presek P, Kroczek R A. Blood 2001; 98: 1047-54). sCD40L acts pro-inflammatory on endothelial cells and promotes the coagulation by inducing the expression of tissue factors by monocytes (Mach F, Schonbeck U, Bennefoy J Y, Pober J S, Libby P. Circulation 1997; 96: 396-9) and endothelial cells (Urbich C, Mallat Z, Tedgui A, Clauss M, Zeiher A M, Dimmeler S. J Clin Invest 2001; 108: 1451-8). In addition, sCD40L contains a KGD-sequence (Graf D, Muller S, Korthauer U, van Kooten C, Weise C, Kroczek R A. Eur J Immunol 1995; 25: 1749-54), a known binding motif that is specific for the predominant platelet-integrin αIIbβ3 (Scarborough R M, Naughton M A, Teng W, et al. J Biol Chem 1993; 268: 1066-73). It could be shown that CD40L indeed represents an αIIbβ3-ligand, a platelet agonist, and is required for the stability of arterial thrombi (Andre P, Prasad K S, Denis C V, et al. Nat Med 2002; 8: 247-52).

These findings stringently show that sCD40L plays an important role in the pathophysiology of acute coronary syndromes. Interestingly, an increase of sCD40L can be detected in serum of patients with acute coronary syndromes (Aukrust P, Muller F, Ueland T, et al. Circulation 1999; 100:614-20). It was reported that apparently healthy women that exhibited elevated plasma concentrations of sCD40L carried an increased risk for cardiovascular events (Schonbeck U, Varo N, Libby P, Buring J, Ridker P M. Circulation 2001; 104: 2266-8). It is the aim of the present invention to examine the predictive value of sCD40L-concentrations with respect to cardiac events and the curing effects of the glycoprotein IIb/IIIa-inhibitor abciximab in patients with acute coronary syndromes, wherein the data base of the CAPTURE-study (c7E3 Anti-Platelet Therapy in Unstable Refractory angina) was used (CAPTURE. Lancet 1997; 349:1429-35).

Inflammatory markers that determine the activity of the disease, possibly before a myocardial necrosis occurs, can represent important additional information for the diagnostic and therapeutic stratification in patients with acute coronary syndromes. The specific therapeutic inhibition of cytokines that are essential for the plaque-stability may be a novel strategy for the treatment of patients with unstable and stable coronary heart disease.

It was recently shown for placental-growth factor (PlGF), a member of the family of the vascular-endothelial-growth factor-family (VEGF-family) of growth factors, that it is upregulated in early and progressed arteriosclerotic lesions.

U.S. Pat. No. 6,225,088 describes PlGF in connection with proliferative diseases, whereas in the WO 92/06194, PlGF is described as an angiogenetic factor.

De Falco et al. (De Falco S, Gigante B, Persico M G. "Structure and function of placental growth factor" Trends Cardiovasc Med 2002 August; 12(6):241-6) describe the association of derogated angiogenesis and arteriogenesis during pathologic conditions, such as, for example, ischemia and tumour formation in mice. Thereby, PlGF is described as an essential factor for the angiogenesis under pathologic conditions. PlGF is proposed as an alternative target for an angiogenetic therapy.

Luttun et al. (Luttun A, Tjwa M, Moons L, Wu Y, Angelillo-Scherrer A, Liao F, Nagy J A, Hooper A, Priller J, De Klerck B, Compernolle V, Daci E, Bohlen P, Dewerchin M, Herbert J M, Fava R, Matthys P, Carmeliet G, Collen D, Dvorak H F, Hicklin D J, Carmeliet P. Revascularization of ischemic tissues by PlGF treatment, and inhibition of tumour angiogenesis, arthritis and atherosclerosis by anti-Flt1 Nat Med 2002 August; 8(8): 831-40) describe therapeutic methods of PlGF and Flt-1 in the context of angiogenesis. It is furthermore described that inhibition of PlGF reduces the growth and vulnerability of arteriosclerotic plaques.

Oura et al. (Oura H, Bertoncini J, Velasco P, Brown L F, Carmeliet P, Detmar M. A critical role of placental growth factor in the induction of inflammation and oedema formation. Blood 2003 Jan. 15; 101(2): 560-7) describe the role of PlGF in cutaneous inflammation and angiogenesis. Furthermore, the effects of elevated and reduced levels of PlGF and their comparison with the status of the inflammation are described.

The pro-inflammatory cytokine CD40L is released by activated platelets. The soluble form of CD40L, namely sCD40L, is increasingly present in patients with acute coronary syndromes. Thus, the prognostic value of sCD40L as a marker for the activation of platelets was also examined in view of the therapeutic effect of an inhibition of the glycoprotein IIb/IIIa-receptor.

Pregnancy-associated plasma protein-A (PAPP-A) is a high molecular weight zinc-binding matrix-metalloproteinase, belonging to the metzincin-superfamily of metalloproteinases, and was initially identified in the plasma of pregnant women. It is broadly used for the screening of foetal trisomy in the first trimester of gestation. It was also recently found for PAPP-A that it is expressed in eroded and loosened plaques, respectively, but is only minimally expressed in stable plaques, and in those wherein a re-occurrence with symptoms as in patients with ACS is assumed. Nevertheless, the exact role of circulating PAPP-A plasma levels for the prediction of hard endpoints, such as death or myocardial infarction, is not exactly determined in patients with ACS. In addition, it is completely unknown whether PAPP-A plasma levels provide additional prognostic information in patients with ACS compared to recently established biomarkers. Therefore, the inventors compared the prognostic significance of PAPP-A plasma levels with markers of systemic inflammation, the activation of platelets, ischemia, and myocardial necrosis in patients with ACS.

Many different molecular markers can be found in the state of the art that can be suitable for the diagnosis of a cardiovascular disease. Examples of such markers are, amongst others:

Pregnancy-associated plasma protein A (PAPP-A); C-reactive protein (CRP); hs-CRP; placental growth factor (PlGF); interleukin-18 (IL-18/IL-18b); brain natriuretic peptide (BNP); NT-pro brain natriuretic peptide (NT-proNP); sCD40L, cTnI/T, IL-10, ICAM-1, VCAN-1, E-selectin, P-selectin, IL-6, VEGF, serum amyloid A (SAA), CKMB, MPO, LpPLAz, GP-BB, IL1RA, TAF1, soluble fibrin, anti-oxLDL, MCP-1, tissue factor (TF), MMP-9, Ang-2, Tffi-2, IL-P, bFGF, PCM, and VEGF-A.

Some of the above indicated markers are markers known and characterised for the examination of coronary diseases, nevertheless, others have not yet been correspondingly examined.

Nearly all of the given markers have a diagnostic value with respect to certain cardiovascular events. TnT, for example, is of particular value for the diagnosis and the prediction of MI (see above). Inflammatory markers, such as CRP, are valuable for the diagnosis and prediction of an inflammation that can lead to a plaque-rupture and MI.

Many of the above indicated markers have a diagnostic value for cardiovascular diseases. The use of a combination of markers was described only very conservatively.

Lund et al. in Circulation. 2003, 108:1924-1926, describe the combination of PAPP-A with TnI (troponin I); Peng et al. in Clinica Chimica Acta 319 (2002) 19-26, describe the combination of sCD40L with sICAM-1 and sVCAM-1. Lenderink et al. in European Heart Journal (2003) 24, 77-85, describe the combination of TnT with CRP. Heeschen et al. in Journal of the American College of Cardiology; Vol. 35, No. 6, 2000, mention the combination of TnT with CRP.

Heeschen et al. in Circulation. 2003; 107:2109-2114, describe the combination of TnT, CRP and IL-10. Blankenberg et al. in Circulation. 2002; 106:24-30, describe the combination of CRP and IL-6. Autiero et al. in Journal of Thrombosis and Haemostasis, 1:1356-1370, describe the combination of PlGF and VEGF.

However, until now the potential of the improved analysis by the combination has neither been examined, nor was the development of selective superior marker-assays completed. Which markers are suitable for an effective diagnosis therefore can not be readily derived from the above indicated publications.

In view of the above, it is therefore an object of the present invention to provide a method by which the risk of an adverse cardiovascular event being due to coronary thrombosis can be estimated with the aid of an individual risk profile. It is a further object of the present invention to develop a method for the evaluation of the probability, whether a treatment with an active ingredient for the inhibition of the placental growth factor (PlGF) is advantageous. With the aid of this method the attending physician shall be, better than before, enabled to select suitable measures in order to positively influence the patients and/or to prevent an adverse event, or to at least reduce it in its severity for the affected patients.

It is the object of the present invention to develop a method by which the risk to suffer from an adverse cardiovascular event being due to a coronary thrombosis can be estimated with the aid of an individual risk profile. This shall be done by measuring the concentration of a marker of the activation of platelets. It is furthermore an object of the present invention to develop a method for evaluating the probability, whether a treatment with an active ingredient for the inhibition of the activation of platelets is advantageous. With the aid of this method the attending physician shall be, better than before, enabled to select suitable measures in order to positively influence the patients and/or to prevent an adverse event, or to at least reduce it in its severity for the affected patients.

It is a further object of the present invention to find general combinations of diagnostic markers for cardiovascular events that allow for a precise diagnosis which cardiovascular event the patient had already suffered from, and from which he will possibly suffer in the future. It is a particular object to find marker combinations that can advantageously be performed in parallel. Ideally, these measurements would allow for measuring patients with chest pain, simultaneously with TnT.

The object of the present invention is solved by a method for analysing samples in association with acute cardiovascular diseases. The method according to the invention comprises the steps of: (a) obtaining a biological sample to be analysed from a subject; (b) determining of the concentration of at least one marker selected from soluble CD40-ligand (sCD40L), PAPP-A, and PlGF, (c) optionally, determining of the concentration of at least one additional marker selected from troponin T (TnT), MPO, NT-proBNP, VEGF, BNP, and additional inflammatory markers, and (d) comparing the results that are obtained for the sample to be analysed with reference value/s and/or the values from reference samples.

The markers that are used for the analysis in the context of the present invention are, to the largest part, markers that are well known and characterised from the state of the art, that, however, until now were only insufficiently characterised for the use in a diagnosis of an acute cardiovascular disease.

Thus, C-reactive protein (CRP) and hsCRP are characterised as markers of systemic inflammation, troponin cTn1/T is characterised as marker for necrosis; the pregnancy associated plasma protein A (PAPP-A) is characterised as a marker for the activation of macrophages; IL-10 (Interleukin 10) is characterised as a marker for the inflammatory balance, sCD40L is characterised as a marker for the thrombo-inflammatory activation, MPO (myeloperoxidase) is characterised as a marker for oxidative stress, placental growth factor (PlGF) is characterised as a marker for vascular inflammation, and the markers brain natriuretic peptide (BNP) and NT-pro brain natriuretic peptide (NT-proNP) are characterised as markers of neurohumoral activation and ischemia.

Other similar and also useful markers are interleukin-18 (IL-18/IL-18b), ICAM-1, VCAN-1, E-selectin, P-selectin, IL-6, VEGF, serum amyloid A (SAA), CKMB, LpPLAz, GP-BB, IL-1RA, TAF-1, soluble fibrin, anti-oxLDL, MCP-1, tissue factor (TF), MMP-9, Ang-2, Tffi-2, bFGF, PCM, and VEGF-A.

WO 03/040692 (and Circulation 2001; 104:2266-2268) describes that sCD40L can be advantageously used in combination with an inflammatory marker, in particular CRP. However, this combination is exclusively used for the diagnosis of non-acute cardiac diseases, due to doubtful results a stratification is rejected by WO 03/040692.

Preferred is a method according to the invention, wherein the sample to be analysed and/or the reference sample is derived from a mammal, in particular from a human. Further preferred is a method according to the invention, wherein the sample to be analysed and/or the reference sample is selected from the group consisting of peripheral blood or fractions thereof, and cell culture suspensions or fractions thereof. It if further preferred that the sample to be analysed and/or the reference sample is blood serum or blood plasma. Peripheral whole blood is particularly preferred as a sample to be analysed and/or reference sample.

According to a further aspect of the method according to the invention, the sample to be analysed and/or the reference sample can be pre-treated, wherein, e.g., a coagulation inhibitor, in particular heparin, is added to said peripheral blood.

In accordance with the invention, it could surprisingly be found that, in addition to the individual analysis of several of the above-mentioned markers, also combinations of such markers are possible for a diagnosis or monitoring of acute cardiac events, allowing for a markedly improved analysis. In doing so, combinations of markers could be identified as particularly preferred that relate to different aspects of the adverse cardiac event, but can be analysed simultaneously (that is, simultaneously or in a more or less timely spaced series of measurements). In one aspect of this invention, additional markers are selected from inflammatory markers, such as, for example, from CRP, (hs)CRP, and IL-10.

According to a further aspect of the method according to the invention, the markers and combinations thereof as analysed are selected from sCD40L; PAPP-A; PlGF; sCD40L+TnT; PAPP-A+TnT; PlGF+TnT; sCD40L+PAPP-A; sCD40L+PlGF; PAPP-A+PlGF; sCD40L+PAPP-A+TnT; sCD40L+PlGF+TnT; PAPP-A+PlGF+TnT; sCD40L+PAPP-A+PlGF; and sCD40L+PAPP-A+PlGF+TnT. Then, preferred is the further combination with at least one of the additional markers MPO, NT-proBNP, BNP, CRP, (hs)CRP, and IL-10.

Then, particularly preferred according to the invention is a method, wherein the markers and combinations thereof as analysed are selected from CRP, TnT, PAPP-A; CRP, TnT, PAPP-A, IL-10; CRP, TnT, PAPP-A, IL-10, sCD40L, and TnT, PAPP-A, IL-10, sCD40L, VEGF.

The method as used according to the invention for determining the concentrations of the markers as analysed can be selected from all suitable methods for detecting proteins in biological samples that are known to the person of skill in the art. In the context of the present invention, the actual method is not important as long as the method is sensitive enough in order to fall below the detection level that is required for an accurate determination of the concentrations of the markers. Suitable methods are normally based on the binding of a label to the marker to be determined, and the subsequent detection of this label. Thereby, the binding can be covalent or non-covalent and/or occur directly or indirectly. Suitable methods for measuring according to the present invention include, e.g., electro-chemiluminescence. Turbidimetry, nephelometry, and latex-enhanced turbidimetry or nephelometry can also be used.

Due to its high sensitivity and the fact that these methods can also be adapted to highthroughput-environments, according to the invention methods are preferred, wherein the determining of the concentration takes place by means of an immunological method by means of marker-binding molecules. Examples for such methods are ELISA (enzyme-linked immunosorbent assay), sandwich enzyme immunoassays or solid-phase immunoassays. Preferred is therefore that the marker-binding molecules are selected from the group consisting of antimarker-antibodies or parts thereof, and marker-receptors or parts thereof.

These molecules can be selected from a very large multitude of marker-specific molecules. It is preferred that the marker-binding molecules are selected from the group consisting of antibodies that are specifically directed against markers or against parts thereof, or parts or fragments thereof, and a marker-receptor or parts thereof, or an integrin, e.g. the platelet-integrin αIIbβ3 or parts thereof. Particularly preferred is a method according to the invention, wherein the antibodies, parts or fragments thereof comprise polyclonal antibodies, monoclonal antibodies, Fab-fragments, scFv-antibodies, and diabodies.

According to a further aspect of the method of the present invention components of the method can be present bound to a solid phase, thus, the marker-binding molecules can be present in solution or matrix-immobilised. A multitude of materials that are known to the person of skill are used as matrices, such as, for example, resin-matrices and/or common columnmatrices. Particularly preferred is furthermore a method according to the invention, wherein the marker-binding molecules are coupled to one or several detection molecules from the group consisting of fluorescein thioisocyanate, phycoerythrine, enzymes (for example horseradish-peroxidase), and magnetic bead.

According to a further aspect of the method according to the invention, the marker-binding molecules can be detected with an antibody that is coupled to one or several detection molecules. Thus, this represents an indirect detection of the binding of the molecule. Such two-step detections are very well known to the person of skill, for example, from the technology of anti-antibody-detection.

According to a further aspect of the method of the present invention, immunocytological methods can be used for the analysis of the sample. For this, all methods are suitable that allow for a specific determination based on the marker/molecule-interaction. Preferred are methods that are selected from the group consisting of sandwich-enzyme-immunoassay, ELISA, and solid phase immunoassays.

The results that are obtained for the samples to be analysed are usually compared with a reference sample. Which sample can serve as a reference sample will, in particular, depend from the kind of the sample that is analysed, and the history of the disease of the individual from which the sample to be analysed is derived. Preferred is a method according to the invention, wherein the reference sample is derived from one or the mean value of several mammals, wherein a cardiovascular disease was excluded. Nevertheless, this is not mandatory, if, e.g. the progression of a disease shall be determined, also an "old" sample of the same patient can be used as a reference sample. It will be obvious for the person of skill, which samples are suitable as reference samples for the method according to the invention.

According to a further aspect of the method according to the present invention, the acute cardiovascular diseases that are to be diagnosed and/or prognosed, and/or whose therapy shall be monitored can be selected from the group consisting of unstable angina, myocardial infarction, acute heart syndromes, coronary arterial disease, and heart insufficiency. Nevertheless, it shall not be excluded that the method according to the invention is suitable for and can be employed in additional acute cardiac disease conditions.

A further aspect of the present invention relates to a diagnostic kit, wherein said kit comprises means for performing the method according to the invention, optionally together with additional components and/or excipients. Preferably, such means are at least one antibody for detecting of markers, and means for the subsequent quantification of said markers. In addition, the kit can contain other components and/or enzymes for performing the method according to the present invention, e.g. instruction manuals for an interpretation of the results of the assays in view of the risk profile of the patient, and corresponding countermeasures and proposals for therapy.

It is preferred to perform the method according to the invention with the aid of a diagnostic kit that comprises gold-labelled polyclonal mouse-indicator antibodies, biotinylated polyclonal detection antibodies, and an assay device comprising a fibreglass-fleece.

A further aspect of the present invention thus relates to the use of the method according to the invention for the diagnosis and/or prognosis of acute cardiovascular diseases, and/or for monitoring of their therapy. This is done by the quantitative and critical determination of markers. Based on the risk profile that then can be generated, suitable countermeasures can then be performed by the attending physician in order to positively influence the patients and to prevent the adverse event or at least to reduce it in its severity for the affected patient. Such a therapy according to the invention can, e.g., comprise the administration of statines or inhibitors of the glycoprotein IIb/III-receptor, in particular abciximab. However, the person of skill is aware of further possible therapies in accordance with a common scheme in order to treat cardiovascular diseases that can occur.

In a further embodiment of the invention, an anti-inflammatory means is co-administered. Said means can be selected from non-steroid or steroid anti-inflammatory means that, e.g., can include: alclofenac; alclometason; dipropionate; algestonacetonide; alpha-amylase; amcinafal; amcinafid; amfenac sodium; amiprilose hydrochloride; anakinra; anirolac; anitrazafen; apazon; balsalazid disodium; bendazac; benoxaprofen; benzydamine hydrochloride; bromelain; broperamol; budesonide; carprofen; cicloprofen; cintazon; cliprofen; clobetasolpropionate; clobetasonbutyrate; clopirac; cloticasonpropionate; cormethasonacetate; cortodoxon; deflazacort; desonid; desoximetason; dexamethasondipropionate; diclofenac potassium; diclofenac sodium; diflorasondiacetate; diflunudon sodium; diflunisal; difluprednat; diftalon; dimethylsulfoxide; drocinonid; endryson; enlimomab; enolicam sodium; epirizol; etodolac; etofenamat; felbinac; fenamol; fenbufen; fenclofenac; fenclorac; fendosal; fenpipalon; fentiazac; flazalon; fluazacort; flufenamine acid; flumizol; runisolidacetate; plunixin; flunixin meglumine; fluocortin butyl; fluorometholonacetate; fluquazon; flurbiprofen; fluretofen; fluticasonpropionate; puraprofen; furobufen; halcinonid; halobetasolpropionate; halopredonacetate; ibufenac; ibuprofen; ibuprofen aluminium; ibuprofen piconol; ilonidap; indomethacin; indomethacin sodium; indoprofen; indoxol; mitrazol; isoflupredonacetate; isoxepac; isoxicam; ketoprofen; lofemizol hydrochloride; lomoxicam; loteprednol etabonat; meclofenamat sodium; meclofenamine acid; meclorison dibutyrate; mefenamin acid; mesalamine; meseclazon; methylprednisolon suleptanate; momiflumat; nabumeton; naproxen; naproxen sodium; naproxol; nimazon; olsalazin sodium; orgotein; orpanoxin; oxaprozin; oxyphenbutazon; paranylin hydrochloride; pentosan polysulfat sodium; phenbutazon sodium glycerate; pirfenidon; piroxicam; piroxicam cinnamate; piroxicam olamine; pirprofen; prednazat; prifelon; prodolinic acid; proquazon; proxazol; proxazolcitrate; rimexolon; romazarit; salcolex; salnacedin; salsalat; salicylates; sanguinariumchloride; seclazon; sermetacin; sudoxicam; sulindac; suprofen; talmetacin; talniflumat; talosalat; tebufelon; tenidap; tenidap sodium; tenoxicam; tesicam; tesimid; tetrydamine; tiopinac; tixocortol pivalat; tolmetin; tolmetin sodium; triclonid; triflumidate; zidometacin; glucocorticoides; zomepirac sodium.

In the context of the present invention, "diagnosis" relates to the ascertaining, whether an individual has suffered from a particular cardiovascular event. In the context of the present invention, "prognosis" relates to the prediction of the probability (in %) whether an individual will suffer from a particular cardiovascular event. In the context of the present invention, "stratification of the therapy" relates to the determination of the suitable therapeutic treatment for said cardiovascular event that will occur or has occurred. In the context of the present invention, "monitoring of the therapy" relates to the control and, optionally, an adjusting of the therapeutic treatment for an individual. In the context of the present invention, "therapeutic treatment" includes all treatments that possibly improve the pathophysiological condition of an individual, and, e.g., includes the administration of pharmaceutics as well as chirurgical treatment (e.g. balloon dilatation).

Base line-values of the sCD40L-concentration make available information of prognostic value in patients with acute coronary syndromes, independently of the occurrence of a myocardial necrosis. In addition, the high risk group of patients that can gain the largest benefit from an anti-platelet-treatment with abciximab can be identified by means of sCD40L.

The present study provides direct evidence for the fact that sCD40L is an informative biochemical marker of an activation of platelets. An increase of the concentration of CD40L reliably identifies a specific subgroup of patients with acute coronary syndromes that carry a profound risk to suffer from a cardiac event, and that gain the largest benefit from treatment with the glycoprotein IIb/IIIa-receptor-antagonist abciximab. Correspondingly, CD40L does not only essentially contribute to the pathophysiology of acute coronary syndromes, but provides a reliable and informative clinical marker by which patients having a formation of high risk-lesions and/or coronary thrombosis can be identified (Andre P, Prasad K S, Denis C V, et al., Nat Med 2002; 8:247-52; Andre P., Nannizzi-Alaimo L, Prasad S K, Phillips D R.; Circulation 2002; 106: 896-9).

In 40.5% of the CAPTURE-patients, the sCD40L-concentrations in the circulation were present above the calculated threshold concentration of 5.0 µg/l. These patients having an elevated sCD40L-concentrations carry a profound cardiac risk to experience a lethal or non-lethal myocardial infarction. This elevated cardiac risk in patients with high sCD40L-concentrations receiving a placebo was particularly obvious during the first 72 hours (FIG. 5a). However, the frequency of the events during the whole six months developed further apart (FIG. 5b). sCD40L could be found as an informative prognostic marker being independent from the detection of a myocardial necrosis and independent from the inflammatory markers CRP and TNF-α as well as from the adhesion molecule ICAM-1. TnT, CRP, and sCD40L provided reliable prognostic information in a multivariate regression model (Table 2). Using the sCD40L-concentration, patients without indications of a myocardial necrosis were identified that exhibited an increased cardiac risk. By using predetermined threshold concentrations for TnT and CRP together with a classification of the patients based on the number of cardiac markers that were elevated it was found that a simultaneous estimation of these pathobiologically different biochemical markers at the time where the patient is admitted allows for an informative prediction of the risk of the patient to suffer from an adverse cardiac event during the following six months.

Troponines represent markers of a myocardial necrosis, nevertheless, they are not actively involved in the pathophysiology of acute coronary syndromes. Rather, they are surrogate markers for the fragile formation of thrombi (Lindahl B, Diderholm E, Lagerqvist B, Venge P, Wallentin L; J Am Coll Cardiol 2001; 38:979-86; Heeschen C, van Den Brand M J, Hamm C W, Simoons M L; Circulation 1999; 100:1509-14; Benamer H, Steg P G, Benessiano J, et al.; Am Heart J 1999; 137:815-20). In post mortem-studies on patients with acute coronary syndromes, an erosion or rupture of the fibrous caps of the arteriosclerotic plaques that are the basis of the pathophysiology was identified (Lindahl B, Diderholm E, Lagerqvist B, Venge P, Wallentin L; J Am Coll Cardiol 2001; 38:979-86; Heeschen C, van Den Brand M J, Hamm C W, Simoons M L; Circulation 1999; 100:1509-14). An exposure of components of the plaques, collagen and other components of the vascular wall leads to an increase of the vascular tonus and the activation of platelets (Farb A, Burke A P, Tang A L, et al.; Circulation 1996; 93:1354-63; Davies K T, Thomas A C; Br Heart J 1985; 53:363-73; Davies M J; N. Engl J Med 1997; 336:1312-4). The thrombotic embolism of a coronary artery with increased microvascular perfusion and necrosis is an essential component of acute coronary syndromes (Heeschen C, van Den Brand M J, Hamm C W, Simoons M L; Circulation 1999; 100:1509-14; Benamer H, Steg P G, Benessiano J, et al.; Am Heart J 1999; 137:815-20). Correspondingly, sensitive markers, in particular troponines as surrogate markers of an arterial thrombotic embolism that results from an active thrombotic process in the underlying lesion, serve for the detection of a small injury of the myocardium.

In contrast to this, sCD40L could be directly involved in the pathophysiology of acute coronary syndromes in several ways. Recent evidences suggest that CD40L contributes essentially to the progression of an arteriosclerosis, and correspondingly to a destabilisation of arteriosclerotic plaques (Mach F, Schonbeck U, Sukhova G K, Atkinson E, Libby P; Nature 1998; 394:200-3; Lutgens E, Gorelik L, Daemen M J, et al.; Nat Med 1999; 5:1313-6). It was proposed that CD40/CD40L-interactions promote complications by atheroms in that they induce the expression of cytokines, chemokines, growth factors, matrix-metalloproteinases, and procoagulants in different atherom-associated cellular types (Schonbeck U, Libby P.; Cell Mol Life Sci 2001; 58:4-43; Henn V, Slupsky J R, Grafe M, et al.; Nature 1998; 391:591-4; Henn V, Steinbach S, Buchner K, Presek P, Kroczek R A; Blood 2001; 98:1047-54; Mach F, Schonbeck U, Bonnefoy J Y, Pober J S, Libby P.; Circulation 1997; 96:396-9; Miller D L; Yaron R, Yellin M J; J Leukoc Biol 1998; 63-373-9; Kotowicz K, Dixon G L, Klein N J, Peters M J, Callard R E; Immunology 2000; 100:441-8). Novel studies have shown that, in addition to leukocytes and non-leukocytic cells including granulocytes, mononuclear phagocytes, endothelial cells and cells of the smooth musculature (Schonbeck U, Libby P; Cell Mol Life Sci 2001; 58:4-43), activated platelets produce and release large amounts of sCD40L (Henn V, Steinbach S, Buchner K, Presek P, Kroczek R A; Blood 2001; 98:1047-54). Another study shows that a cardiopulmonary bypass causes an increase of the concentration of sCD40L in plasma that corresponds to a decrease of the content of CD40L in platelets, suggesting that sCD40L primarily is derived from the platelets and could contribute to the thrombotic complications that are related to such a bypass (Nannizzi-Alaimo L, Rubenstein M H, Alves V L, Leong G Y, Phillips D R, Gold H K; Circulation 2002, 105:2849-2854). It was furthermore found that sCD40L positively correlates with soluble P-selectin in plasma and 11-dehydrothromboxane $B_2$-concentrations in urine (Cipollone F, Mezzetti A, Porreca E, et al.; Circulation 2002; 106:399-402). In addition, experimental analyses showed that CD40L is required for a stabilisation of arterial thrombi (Andre P, Prasad K S, Denis C V et al.; Nat Med 2002; 8:247-52). The present study now provides direct evidence for the fact that CD40L indeed is a marker of the activation of platelets. The activation of platelets as determined by flow cytometry in patients with acute coronary syndromes correlated significantly with the concentrations of sCD40L in serum (FIG. 7). Interestingly, sCD40L was found as an independent predictive factor of an activation of platelets with the highest significance. The results of the present study established sCD40L-concentrations as highly informative prognostic markers in patients with acute coronary syndromes that are in danger to suffer from a thrombosis. These findings are supported by the fact that an inhibition of the glycoprotein IIb/IIIa-receptor by abciximab eliminated the increased risk in patients with acute coronary syndromes and elevated sCD40L-concentrations. While troponin positively indicated the tendency of a thrombus to cause an embolism and to lead to myocardial necrosis, elevated concentrations of sCD40L in patients with acute coronary syndromes reflect the thrombotic activity of the triggering lesion to recruit and activate platelets.

It was shown in an earlier analysis of a subgroup of patients of the CAPTURE-study that an additional treatment with the glycoprotein IIb/IIIa-receptor-antagonist abciximab reduced the elevated risk of troponin-positive patients to the extent of troponin-negative patients (Hamm C W, Heeschen C, Goldmann B, et al.; N Engl J Med 1999; 340:1623-9). These patients constitute about ⅓ of the patients with acute coronary syndromes (Hamm C W, Braunwald E; Circulation 2000; 102:118-22; Antman E M, Tanasijevic M J, Thompson B, et al; N Engl J Med 1996; 335:1342-9; Ohman E M, Armstrong P W, Christenson R H, et al.; N Engl J Med 1996;

335:1333-41; Hamm C W, Ravkilde J, Gerhardt W, et al.; N Engl J Med 1992; 327:146-50; Hamm C W, Goldmann B U, Heeschen C, Kreymann G, Berger J, Meinertz T; N Engl J Med 1997; 337:1648-53). Similar findings regarding troponin T and troponin I later resulted from other studies (Newby L K, Ohman E M, Christenson R H, et al.; Circulation 2001; 103:2891-6; Januzzi J L, Chae C U, Sabatine M S, Jong I K; J Thromb Thrombolysis 2001; 11:211-5; Heeschen C, Hamm C W, Goldmann B, Deu A, Langenbrink L, White H D; Lancet 1999; 354:1757-62), and troponines were subsequently included into the novel guidelines as part of the risk stratification in patients with acute coronary syndromes (Hamm C W, Bertrand M, Braundwald E; Lancet 2001; 358:1533-8; Braunwald E, Maseri A, Armstrong P W, et al.; Eur Heart J 1998; 19:D22-30). It is shown in the present study that such a pronounced positive effect of an anti-platelet-therapy is obvious also in patients with elevated sCD40L-concentrations. The present analysis suggests that patients with acute coronary syndromes that exhibit increased concentrations of sCD40L are effectively stabilised by the glycoprotein IIb/IIIa-receptor-antagonist abciximab (FIGS. 5a, b). At a calculated threshold concentration of 5.0 µg/l, an abrupt change of the risk quotient of 0.87 for the second quintile, and 1.12 for the third quintile towards significantly lower values of 0.36 for the fourth quintile, and 0.38 for the fifth quintile, respectively, (FIG. 4) was observed. Interestingly, the concentrations of TnT and sCD40L provided independent predictive values with respect to both the risk of ischemic events as well as the positive effect of a glycoprotein IIb/IIIa-receptor-inhibition by abciximab. Patients without indications of a myocardial injury (troponin-increase is lacking) which, nevertheless, exhibited increased concentrations of sCD40L, gained a substantial benefit from the treatment with the glycoprotein IIb/IIIa-inhibitor abciximab. Thus, patients with a high risk for a thrombosis of the coronary vessels, as proven either by an increase of the sCD40L-concentration or an increase of the TnT-concentration, which finally made up 54% of the overall patients involved the CAPTURE-study, had a pronounced advantage from the treatment with abciximab, with a risk quotient of 0.38 [0.21-0.72]; p<0.001).

In summary, it can be stated that the present study documents the important and independent role of sCD40L as a marker of the activation of platelets for the diagnostic and therapeutic risk stratification. The increased cardiac risk of patients with high sCD40L-concentrations that received a standard therapy with heparin and aspirin was reverted by the glycoprotein IIb/IIIa-receptor-antagonist abciximab. The combined use of troponines and sCD40L that both represent essential components of the pathophysiology in patients with acute coronary syndromes provides important insights into the activity of the disease, the cardiologic risk, and the effectiveness of a treatment by means of glycoprotein IIb/IIIa-inhibition by abciximab being superior to the use of a single marker.

The results of the present study establish the PlGF serum level as a novel and effective independent prognostic determinant of the clinical outcome in patients with acute coronary syndromes. It has to be particularly noted that in patients with lower hsCRP serum levels elevated PlGF serum levels identify a subgroup of patients that suffer from a significantly increased cardiac risk (fitted hazards-ratio 3.58 [95% CI 1.48-7.72]; p=0.001).

The predictive value of PlGF serum levels is independent from evidence for myocardial necrosis as determined by the troponin serum level. Finally, elevated PlGF serum levels not only identify those patients with acute chest pain that develop acute coronary syndromes, but also those patients that suffer from an increased risk of reoccurring instability from an initial acute coronary syndrome after discharge. Thus, measuring of the PlGF serum levels can not only be a reliable and effective clinical tool for the identification of patients with high risk formation of lesions but also of persistent vascular inflammation of the coronary circulation.

The role of PlGF as a primary inflammatory marker of the instability of arteriosclerotic lesions can be explained by its well documented pro-inflammatory effects in animal models of arteriosclerosis or arthritis [Luttun A, Tjwa M, Moons L, et al. Revascularization of ischemic tissues by PlGF treatment, and inhibition of tumor angiogenesis, arthritis and atherosclerosis by anti-Flt1. Nat Med 2002; 8(8):831-40]. Although PlGF belongs to the family of VEGF, its etiopathogenetic role appears to be associated rather with inflammation as with angiogenesis [Luttun A, Tjwa M, Moons L, et al. Revascularization of ischemic tissues by PlGF treatment, and inhibition of tumor angiogenesis, arthritis and atherosclerosis by anti-Flt1. Nat Med 2002; 8(8):831-40.]. Indeed, whilst the VEGF-increase due to hypoxia and the increase of the VEGF-serum level are regarded as an early adaptation of the myocardium to the decreasing bloodflow [Lee S H, Wolf P L, Escudero R, Deutsch R, Jamieson S W, Thistlethwaite P A. Early expression of angiogenesis factors in acute myocardial ischemia and infarction. N Engl J Med 2000; 342(9):626-33.], PlGF is not affected or down-regulated by hypoxia [Khaliq A, Dunk C, Jiang J, et al. Hypoxia down-regulates placenta growth factor, whereas fetal growth restriction up-regulates placenta growth factor expression: molecular evidence for "placental hyperoxia" in intrauterme growth restriction. Lab Invest 1999; 79(2):151-70, Cao Y, Linden P, Shima D, Browne F, Folkman J. In vivo angiogenic activity and hypoxia induction of heterodimers of placenta growth factor/vascular endothelial growth factor. J Clin Invest 1996; 98(11):2507-11.]. In agreement with these data, the results of this study do not result in a correlation between the PlGF serum level and the troponin T serum level as a marker of myocardial necrosis, whereas the VEGF serum level positively correlated with the troponin T serum level. In agreement with this, PlGF did not correlate with the VEGF serum level.

Therefore, the PlGF serum level appears not to be affected by myocardial necrosis. In contrast, the VEGF serum levels are coupled with an increase of troponin T, affected TIMI flow, and clinical signs of myocardial ischemia [Heeschen C, Dimmeler S, Hamm C W, Boersma E, Zeiher A M, Simoons M L. Prognostic significance of angiogenic growth factor serum levels in patients with acute coronary syndromes. Circulation 2003; 107:524-530.]. The PlGF serum level being insensitive versus smaller myocardial injuries could specifically be important in patients with acute coronary syndromes, out of which about one third at presentation are positive for troponin [Hamm C W, Braunwald E. A classification of unstable angina revisited. Circulation 2000; 102(1): 118-22.].

Similarly, a myocardial injury could also compromise the value of the hsCRP serum level in order to be able to predict the outcome in patients with acute coronary syndromes. As a classical unspecific downstream acute-phase-marker, the hsCRP serum levels in patients with myocardial injury are increased as measured by an increase of troponin T. It is well established that elevated serum levels of hsCRP are found before the occurrence of a marker of myocardial necrosis in nearly all patients in which an unstable angina occurs before an infarction [Liuzzo G, Baisucci L M, Gallimore J R, et al. Enhanced inflammatory response in patients with preinfarction unstable angina. J Am Coll Cardiol 1999; 34(6): 1696-703.]. The specificity of elevated hsCRP serum level confirming an enhanced vascular inflammation in the presence of myocardial injury is therefore very limited.

Thus, elevated hsCRP serum levels in troponin-positive patients can only represent an elevated risk secondary to myocardial injury as a surrogate marker for thrombotic embolism that rather is derived from an active thrombotic process within the culpritic lesion than from a persisting vascular inflammation.

Indeed, when each of troponin T and VEGF as markers of myocardial necrosis and ischemia are included into a multivariate analysis, elevated hsCRP serum levels are no longer predictive for an elevated risk in patients with acute coronary syndromes.

More important, the reported prevalence of elevated hsCRP serum levels varies considerably in acute coronary syndromes. (more than 30% of the patients with severe unstable angina and more than 50% of the patients with an acute myocardial infarction do not exhibit elevated hsCRP serum levels). Elevated hsCRP serum levels are lacking in more than 30% of patients with severe unstable angina and in more than 50% of those with an acute myocardial infarction that does not follow after an unstable angina [Liuzzo G, Baisucci L M, Gallimore J R, et al. Enhanced inflammatory response in patients with preinfarction unstable angina. J Am Coll Cardiol 1999; 34(6): 1696-703.] suggesting an important heterogenicity of the role of inflammatory triggers of the clinical syndrome of the coronary instability [Libby P, Ridker P M, Maseri A. Inflammation and atherosclerosis. Circulation 2002; 105(9): 1135-43.]. However, it is also well established that individuals can vary in their systemic responses towards a particular inflammatory stimulus [Liuzzo G, Buffon A, Biasucci L M, et al. Enhanced inflammatory response to coronary angioplasty in patients with severe unstable angina. Circulation 1998; 98(22):2370-6, Liuzzo G, Angiolillo D J, Buffon A, et al. Enhanced response of blood monocytes to in vitro lipopolysaccharide-challenge in patients with recurrent unstable angina. Circulation 2001; 103(18):2236-41. Biasucci L M, Vitelli A, Liuzzo G, et al. Elevated levels of interleukin-6 in unstable angina. Circulation 1996; 94(5): 874-7.]. The increase in hsCRP or IL-6 that was observed in response to the vascular trauma induced by balloon dilatation or even by uncomplicated cardiac catheterisation correlates linearly with baseline hsCRP or interleukin-6 serum levels [Liuzzo G, Buffon A, Biasucci L M, et al. Enhanced inflammatory response to coronary angioplasty in patients with severe unstable angina. Circulation 1998; 98(22):2370-6]. In addition, the IL-6 production by monocytes that are isolated from patients with unstable angina significantly increased in patients with elevated hsCRP serum levels, compared to patients with normal hsCRP serum levels [Liuzzo G, Angiolillo D J, Buffon A, et al. Enhanced response of blood monocytes to in vitro lipopolysaccharide-challenge in patients with recurrent unstable angina. Circulation 2001; 103(18):2236-41.]. These individual differences in the extent of the response to a particular inflammatory stimulus can have a genetic basis [Westendorp R G, Langermans J A, Huizinga T W, Verweij C L, Sturk A. Genetic influence on cytokine production in meningococcal disease. Lancet 1997; 349(9069):1912-3.]. Unfortunately, such heterogenic responses limit the utility of downstream acute-phase reactants, such as, for example, hsCRP as inflammatory marker for the risk stratification. In contrast to this, PlGF appears to be a direct proximal stimulus for inflammatory processes within the vascular wall [Luttun A, Tjwa M, Moons L, et al. Revascularization of ischemic tissues by PlGF treatment, and inhibition of tumour angiogenesis, arthritis and atherosclerosis by anti-Flt1. Nat Med 2002; 8(8):831-40.]. Indeed, elevated PlGF serum levels were extremely informative, specifically in patients with acute coronary syndromes, but not non-elevated hsCRP serum levels. In this cohort of patients, elevated PlGF serum levels identified a subgroup of patients with markedly elevated cardiac risk that was similar to the high-risk patients that were defined by elevated troponin serum levels. Thus, elevated PlGF serum levels can indeed represent primary inflammatory indicators of coronary instability.

Furthermore, since the pro-inflammatory effects of PlGF can be specifically inhibited by blocking its receptor Flt-1, these results can also provide an approach for a novel anti-inflammatory therapeutic target in patients with coronary arterial disease [Luttun A, Tjwa M, Canneliet P. Placental Growth Factor (PlGF) and Its Receptor Flt-1 (VEGFR-I): Novel Therapeutic Targets for Angiogenic Disorders. Ann N Y Acad Sci 2002; 979:80-93.]. The pro-inflammatory effects of PlGF can be specifically inhibited by blocking its receptor Flt-1, and provide a novel anti-inflammatory therapeutic option in patients with coronary arterial disease.

The results of the present study show that elevated blood levels of the metalloproteinase PAPP-A are associated with negative outcome in patients with ACS. In agreement with an examination that was performed only recently, the predictive value of PAPP-A plasma levels was most prominent in patients without an increase of troponin. Thus, an elevated PAPP-A plasma level is not only a marker of plaque-instability that promotes the development of ACS but, more important, indicates a bad prognosis, before the occurrence of an acute ischemic event that is caused by plaque-instability. In addition, elevated PAPP-A levels provide additional prognostic information, even in patients with elevated hsCRP plasma levels, suggesting that at least in some patients elevated hsCRP level are not associated with vascular inflammation. The result that the predictive values of PAPP-A were limited to patients with low levels of the anti-inflammatory cytokine interleukin-10 further supports the concept that the balance between pro- and anti-inflammatory cytokines is [important] for the outcome for the patients in ACS. Using a multivariate regression analysis, several biochemical markers, including troponin T, soluble CD40 ligand, interleukin-10, and PAPP-A were identified as independent predictive markers for the outcome for the patients during the subsequent six months of follow-up.

Cardiac troponines are sensitive and specific markers of myocardial necrosis, secondary to thrombotic complications during an acute coronary syndrome, and are highly predictive for the early clinical progression after the outbreak of ACS. However, the risk stratification in troponin negative patients with acute coronary syndrome remains challenging.

About two thirds of the patients with ACS, but without elevations of the ST-segment, exhibit normal values of Troponin, and more than half of the patients exhibit inconclusive electrocardiographical results. During the first weeks following the outbreak of an acute coronary syndrome the risk of mortality or non-fatal myocardial infarction in troponin-negative patients is at about 5 to 8%. Thus, the short term-occurrence of essential cardiovascular events remains relatively substantial in patients without evidences for myocardial necrosis, invoking the need for a further diagnostic processing. A continuous ST-segment monitoring, stress tests, and perfusion imaging methods can be of limited availability for the immediate risk stratification of patients from which it is assumed that they exhibit an acute coronary syndrome. The present study shows that PAPP-A levels indicate a subgroup of patients without elevation of troponin that during the early progression in time after the outbreak of symptoms exhibit an essentially higher risk for cardiac events (72 hours OR 3.17; 30 days: OR 3.33). In contrast to this, the patients without the modifications in the ST-segment that were both negative for TnT and PAPP-A, were subject to a very low risk (0.9% rate of occurrence). Thus, the determination of PAPP-A in patients with ACS is an effective tool for the short term-risk stratification of patients without elevated troponin level.

The progression and the subsequent destabilisation of arteriosclerotic plaques includes important changes in the structure of the arterial wall. The occurrence of a local state of inflammation in patients with ACS is well established as determined by inflammatory markers, such as, for example, CRP. Metalloproteinases are also potential indicators of arterial inflammation, and can contribute to the fragility of the lipid-rich arteriosclerotic plaques by degradation of extracellular matrix, and eventually to its rupture. As described earlier for several other metalloproteinases (MMP-1, MMP-3, MMP-12 or MMP-13) it was found for PAPP-A only very recently that it is expressed in eroded and released plaques, whereas the expression of PAPP-A could not be detected in stable plaques. Other studies have also shown that patients with hyperechonic or isoechoinic carotid plaques exhibit significantly elevated levels of PAPP-A than those with hypoechonic early carotid-lesions. The particular role of PAPP-A in the pathophysiology of ACS remains unclear. It was shown for PAPP-A that it is a specific activator of the insulin-like growth factor-I (IGF-I), a potent mediator of arteriosclerosis. As a matrix-metalloproteinase, PAPP-A could be involved in the processing of the extracellular matrix of plaques, and, consequently, affect the fibrous cap. This leads to a morphology of the plaque that is sensitive against erosion, rupture and subsequent thrombosis. The present study shows that that a single PAPP-A determination, obtained 8.7 hours after the occurrence of the symptoms provides a significant predictive value for the occurrence of death and non-fatal myocardial infarction during the following 6 months follow-up. These data suggest that PAPP-A plays an important pathophysiological role in the destabilisation of the arteriosclerotic plaques during ACS. The production of PAPP-A by activated cells within the arteriosclerotic lesions and its release into the extracellular matrix appears to be tightly associated with the local inflammatory process that occurs within the arterial wall as indicated by the significant positive correlation that was observed between CRP and PAPP-A levels. Indeed, the PAPP-A-levels were highly predictive in patients with elevated CRP levels, whereas in patients with low CRP levels, PAPP-A did not serve as a significant predictor for the outcome of the patients (FIG. 26a). Whilst CRP levels are connected with the troponin-increase, PAPP-A levels appear to be less sensitive against smaller myocardial injury, which could be of particular importance in patients with ACS, out of which at the time of arrival in the hospital about one third are positive for troponin. In addition, PAPP-A levels neither interfered with the predictive power of sCD40L, a marker of the activation of platelets in patients with ACS, nor did they affected these. By multivariate analysis PAPP-A, sCD40L and TnT all were found as independent predictors of adverse outcome (Table 2). A combination of PAPP-A and sCD40L was particularly obvious in patients that were negative for TnT, suggesting that both markers reflect distinct signal pathways reflect that eventually contribute to a pro-inflammatory and pro-coagulating milieu in the coronary circulation. Supporting for a complementary other than a competitive role in order to predict an adverse outcome in patients with ACS are the results of the inventors that the aggressive inhibition of the aggregation of the platelets by abciximab was particularly suitable in patients with elevated sCD40L levels.

In summary, the results of the present invention show that elevated plasma levels of PAPP-A as a marker of the vascular inflammation are associated with an elevated risk for subsequent cardiac events. The predictive value of PAPP-A plasma levels was independent from elevated troponin levels that reflect the actual risk secondary to thrombotic complications that lead to myocardial injury during an acute coronary syndrome. Thus, an elevated PAPP-A plasma level is not only a marker of the plaque instability with respect to the progression to a myocardial infarction, but also indicates a bad prognosis even after the occurrence of an acute ischemic event that is caused by plaque instability.

In summary, it can be stated that the present study documents the important and independent role of PlGF as a marker for the diagnostic and therapeutic risk stratification. The elevated cardiac risk of patients with high PlGF-concentrations that received a standard therapy with heparin and aspirin was reversed by the glycoprotein IIb/IIIa-receptor antagonist abciximab. The combined use of troponines and PlGF which both represent essential components of the pathophysiology in patients with acute coronary syndromes, provides important insights into the activity of the disease, the cardiologic risk, and the effectiveness of a treatment by means of glycoprotein IIb/IIIa-inhibition using abciximab that is superior to the use of a single marker.

In summary, the PlGF serum level represents an effective and reliable biomarker of the vascular inflammation, and negative outcome in patients with acute coronary syndromes. A determination of the PlGF serum levels significantly extends the predictive and prognostic information that is obtained from common inflammatory markers in acute coronary syndromes.

In the following, the invention shall now be further explained based on examples with respect to the attached Figures, but without being limited thereby. In the Figures:

FIG. 1 shows the association between serum concentrations of sCD40L and the incidence of a cardiac event after 24 hours, 72 hours, 30 days, and 6 months in the group of patients that received a placebo (n=544). The patients were grouped into 5 quintiles. The ranges of the sCD40L-concentrations were as follows: 0.003-1.9 µg/l (quintile 1), 1.9-3.5 µg/l (quintile 2), 3.5-5.0 µg/l (quintile 3), 5.0-6.3 µg/l (quintile 4), and >6.3 µg/l (quintile 5). p<0.001 after 72 hours, 30 days, and 6 months.

FIG. 2 shows a diagram according to Kaplan-Meier of the cumulative incidence of myocardial infarction with lethal or non-lethal outcome after 72 hours (a), and 6 months (b) according to the base line-values of the sCD40L-concentration (diagnostic threshold value 5.0 µg/l) in the placebo-group (n=544).

FIG. 3 shows the adapted risk quotient (including 95% confidence interval) in the treatment with abciximab according to the sCD40L-quintiles. A successful treatment is defined as a reduction of lethal or non-lethal myocardial infarction in the course of 6 months. A risk quotient<1.0 indicates the successful treatment with abciximab compared to placebo-treatment.

FIG. 4 shows a Kaplan-Meier-diagram of mortality and non-lethal myocardial infarction 72 hours (a), and 6 months (b) according to the sCD40L-concentration in patients that either received a placebo or abciximab.

FIG. 5 shows the activation of platelets in dependency from the activity of the disease. The activity of platelets as determined by monocyte-platelet-aggregates was significantly increased in patients with stable coronary heart disease. An additional significant increase of the activation of platelets was observed in patients with acute coronary syndromes.

Figure 9:
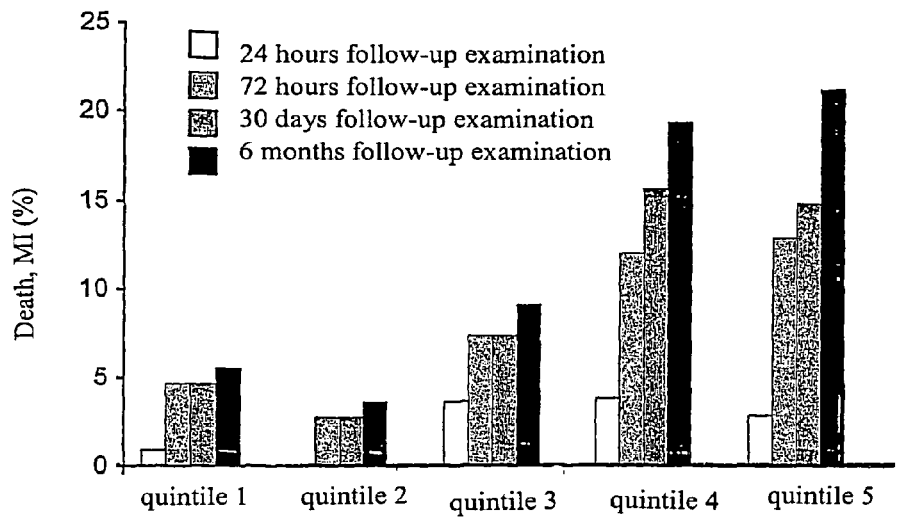

FIG. 9 shows the association between the serum concentrations of PlGF and the incidence of a cardiac event after 24 hours, 72 hours, 30 days, and 6 months in the group of patients that received a placebo (n=547). The ranges of the PlGF-concentrations were as follows: below and identical to 13.3 ng/l (1. quintile), 13.4 to 19.2 ng/l (2. quintile), 19.3 to 27.3 ng/l (3. quintile), 27.4 to 40.0 ng/l (4. quintile), and above 40.0 ng/l (5. quintile). The differences in the rates of an event between the quartiles were significant at 30 days (p 0.001), and 6 months (p<0.001) of follow-up examination.

Figure 10:
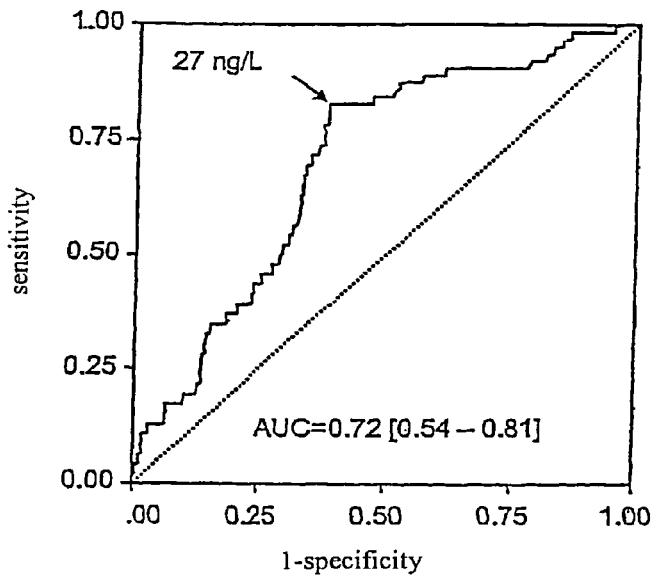

FIG. 10 shows receiver-operating-characteristic curve analysis for the predictive value of PlGF serum levels for the occurrence of mortality or non-lethal myocardial infarction at 6 months follow-up examination.

FIG. 11 shows a diagram according to Kaplan-Meier of the cumulative incidence of myocardial infarction with lethal or non-lethal outcome after 72 hours (a) and 6 months (b) according to the base line-values of the PlGF-serum levels (diagnostic threshold value 27.0 ng/l; n=547).

FIG. 12 shows the predictive value of PlGF for the incidence of myocardial infarction with lethal or non-lethal outcome according to hsCRP serum levels (a), and troponin T serum levels (b). Diagnostic threshold values were 27.0 ng/l for PlGF, 0.1 µg/l for troponin T, and 10 mg/l for hsCRP; n=547).

FIG. 13 shows the predictive value of discharge-PlGF serum levels for the patient-result at 6-months follow-up examination. Patients with elevated PlGF serum levels were subject to a higher cardiac risk, with a rate of occurrence of 7.4%, compared to 2.2% for patients with PlGF serum levels below 27.0 ng/l (p=0.005).

Figure 14:
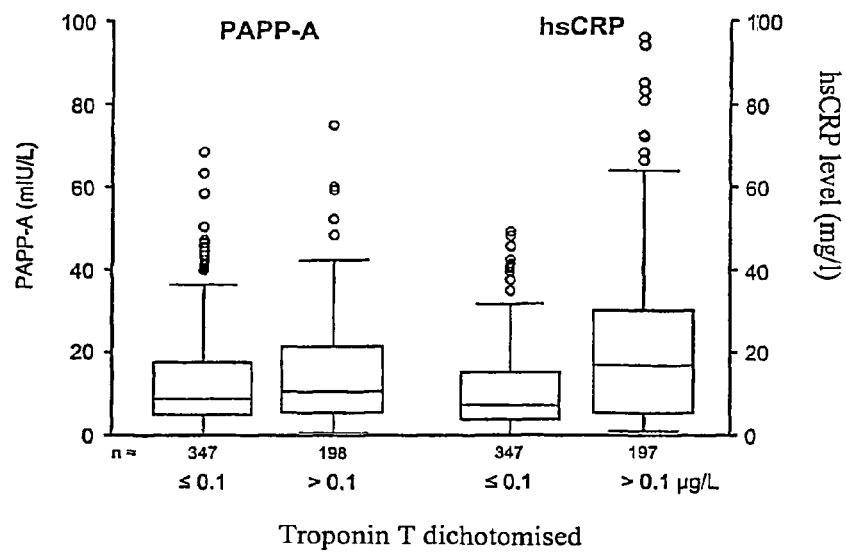

FIG. 14 shows each of the PAPP-A and hsCRP-levels according to the base-line troponin T status. Circles indicate outliers.

Figure 15:
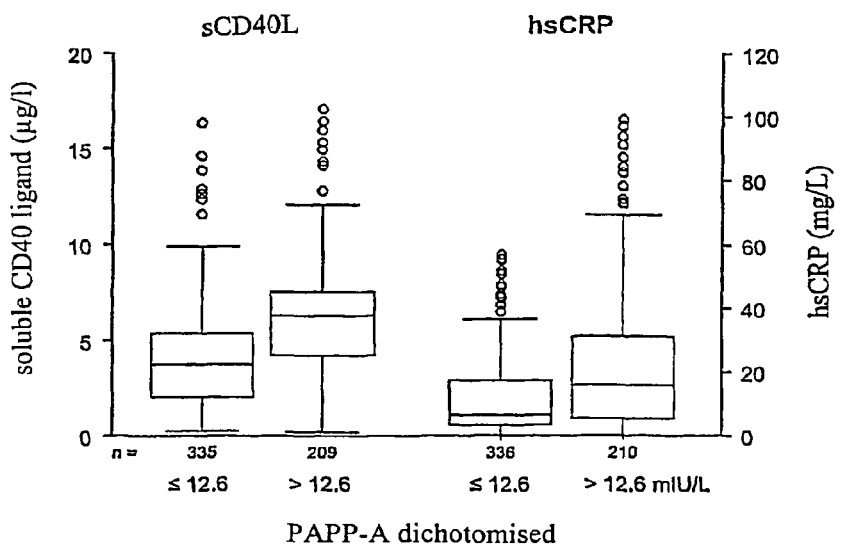

FIG. 15 shows soluble CD40 ligand and hsCRP-levels, respectively, according to the baseline PAPP-A status. Circles indicate outliers.

Figure 16:
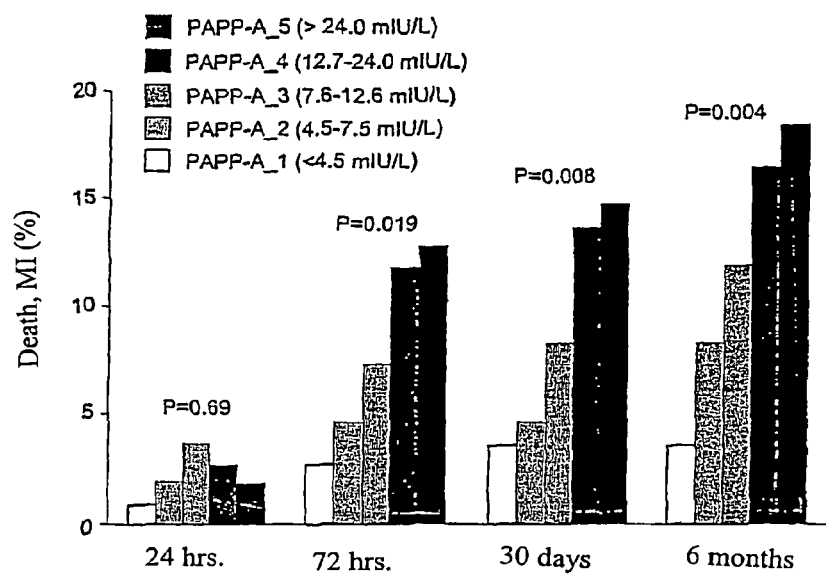

FIG. 16 shows the association between the PAPP-A plasma levels and the rate of cardiac events at 24 h, 72 h, 30 days, and 6 months according to the PAPP-A placebo group (n=547). The ranges of PAPP-A were as follows: (PAPP-A_1)<4.5 mIU/l (n=111); (PAPP-A_2) 4.5-7.5 mIU/l (n=108); (PAPP-A_3) 7.6-12.6 mIU/l (n=109); (PAPP-A_4) 12.7-24.0 mIU/l (n=110) and (PAPP-A_5)>24.0 mIU/l. The in the rates of occurrence were significant at 72 hours (p=0.019), 30 days (p=0.008), and 6 months (p=0.004).

Figure 17:
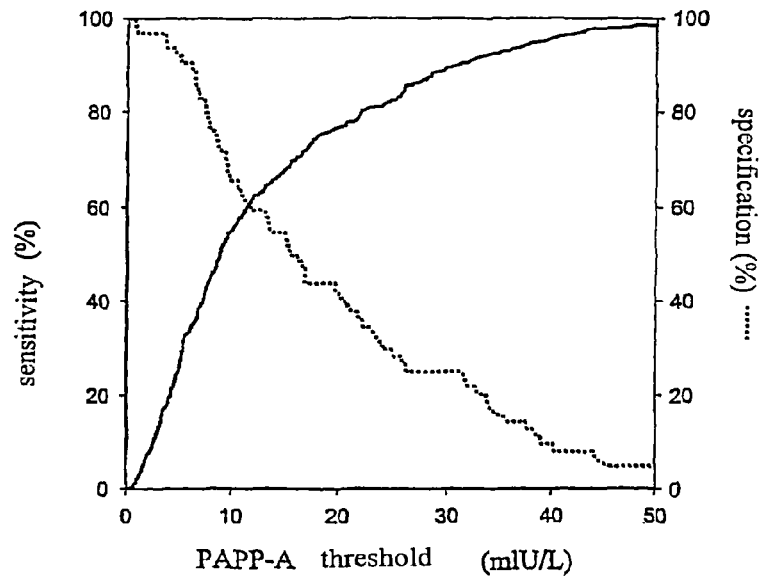

FIG. 17 shows receiver-operating-characteristic curve analysis for the predictive value of PAPP-A plasma levels for the occurrence of mortality or non-lethal myocardial infarction at 6 months follow-up examination.

Figure 18A:
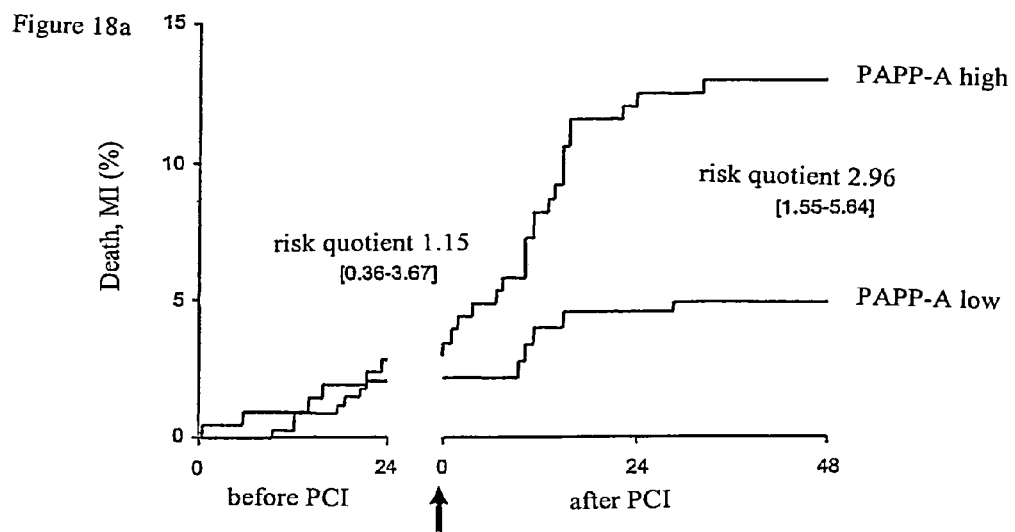

FIG. 18 shows Kaplan-Meier event rate curves that show the cumulative occurrence of death and non-fatal myocardial infarction at 72 hours (a), and 6 months (b) according to PAPP-A baseline plasma levels. Diagnostic threshold value 12.6 mIU/l; n=547

FIG. 19 shows the predictive value of PAPP-A for the occurrence of death and non-fatal myocardial infarction was limited to patients with elevated hsCRP levels (a), and patients with low levels of the anti-inflammatory cytokine IL-10 (b). Diagnostic threshold values 12.6 mIU/l for PAPP-A, 10 mg/l for hsCRP, and 3.5 ng/l for IL-10; n=547

FIG. 20 shows that the predictive value of PAPP-A for the occurrence of death and non-fatal myocardial infarction was particularly informative in patients without troponin T increase (a). In patients that were negative both for TnT and sCD40L, PAPP-A identified a subgroup that suffered from an elevated cardiovascular risk at 6 months follow-up (b). Diagnostic threshold values 12.6 mIU/l for PAPP-A, 0.1 µg/l for TnT, and 5.0 µg/l for sCD40L; n=547

EXAMPLES

I. sCD40L

S1. Patients

Between Mai 1993 and December 1995, the CAPTURE-study registered 1265 patients with refractory unstable angina (61% male, in the age of 61 [48-72, 95% confidence interval]). All CAPTURE-patients were complaining about reoccurring chest pain in the resting state, associated with ECG-modifications during a treatment with intravenous heparin and glycerol trinitrate in an average of 14 hours. The complete patient-population was subjected to a coronary angiography before the occurrence of a markedly coronary arterial disease with triggering lesions of 17% that were suitable for an angioplasty was documented. The patients were randomly assigned to a treatment by abciximab or placebo. The treatment was started within 2 hours after the assignment. Coronary interventions were scheduled in all patients within 18 to 24 hours after the start of the treatment (CAPTURE. Lancet 1997; 349: 1429-35). On average, blood samples (n=1096) were obtained (base line) 8.7 (3.6-11.3) hours after onset of the symptoms.

Primary endpoints of the study were mortality, myocardial infarction, or the necessity for immediate intervention (angioplasty, bypass-surgery of the coronary artery) due to an instability during 30 days or 6 months. In patients that suffered from a heart attack during the period in the hospital, this was accordingly diagnosed, if their values of the enzymatic activity of the creatine kinase in at least two samples was more than three times as high than the upper limit of the normal range, or if their ECG exhibited novel distinct Q-waves in more than two subsequent intervals. This strict definition was chosen in order to exclude any unimportant small increase of the creatine kinase after PTCA. In patients with a myocardial infarction after discharge, this was defined accordingly, if their values of the enzymatic activity of the creatine kinase were more than twice as high than the upper limit of the normal range, or if their ECG exhibited novel distinct Q-waves in two or more subsequent intervals. The secondary endpoint was the symptomatic coronary restenosis of the treated lesion with a diameter of the stenosis of ≥70%, and the necessity for a repeated revascularisation during the subsequent 6 months.

2. Validation of Patients with Acute Chest Pain

A separate group of 626 patients with chest pain (161 women and 465 men, average age 61 [38-82] years) that were presented in the emergency room in a consecutive row with acute chest pain that lasted for less than 12 hours (average 5.1 [2.1-10.4] hours). Patients with a characteristic ST-elevation in the base-ECG or a documented acute myocardial infarction during the preceding 2 weeks were not taken into account. Blood samples were obtained at the time of admission (before the start of treatment), and 4 hours later, kept on ice, centrifuged within 20 minutes after sample collection, and stored at −80° C. for later analysis. It was found that this treatment led to reproducible results during the determination of the sCD40L-concentrations (Nannizzi-Alaimo L, Rubenstein M H, Alves V L, Leong G Y, Phillips D R, Gold H K. Circulation 2002; 105:2849-54). The patients were observed until discharge from the hospital and 30 days thereafter in order to register lethal and non-lethal myocardial infarctions. The presence of a coronary arterial disease was detected through one of the following criteria: ECG-indications of a myocardial ischemia (novel changes in the ST-stretch or inversion of the T-wave), a coronary heart disease in the anamnesis (myocardial infarction or coronary revascularisation, a positive stress test or restriction of the diameter of a main coronary artery by at least 50% in an early angiogram). Patients without coronary heart disease had to show a normal coronary angiogram. The activation of platelets was detected by means of flow cytometry in a subgroup of patients including 131 patients with acute coronary syndromes, 20 patients with stable coronary heart disease, and 10 patients with excluded coronary heart disease.

3. Biochemical Analysis

Plasma samples, anti-coagulated with sodium heparin, were centrally stored at −80° C. The determination of the cardiac markers were performed in the research laboratory of the university Frankfurt without knowledge of the disease history of the patient and the treatment as ordered. The plasma levels of sCD40L (detection limit 0.005 µg/l), soluble P-selectin (0.5 µg/l), tumour necrosis factor-$\alpha$ (TNF-$\alpha$, highly sensitive; 0.12 ng/l), and soluble intracellular adhesion molecule-1 (ICAM-1; 0.35 µg/l) were measured by means of ELISA (R&D systems, Wiesbaden). For a quantification of troponin T (TnT), a one-step enzyme-immunoassay on the basis of the electrochemiluminescence technology (Elecsys 2010, Roche Diagnostics; detection limit 0.01 µg/l) was used. C-reactive protein (CRP) was measured with the aid of the Behring BN II nephelometer (Behring Diagnostics; detection limit 0.2 µg/l).

5. Quantitative Determination of sCD40L

The sCD40L-concentration was determined by using the sandwich-enzyme-immunoassay-technology (R&D Systems, Wiesbaden). A microtitre plate was coated with a polyclonal antibody being specifically directed against sCD40L. Standards and samples were pipetted into the wells, and present sCD40L was bound by the immobilised antibody. After unbound material was washed away, an enzyme-coupled polyclonal antibody that was specifically directed against sCD40L was added to the wells. After a washing step in order to remove unbound antibody-enzyme-reagent, a substrate-solution was added to the wells, and the colour developed in relation to the amount of sCD40L that was bound in the first step. The development of colour was stopped, and the intensity of the colour was measured.

6. Fast Assay for the Detection of CD40L

A fast assay on the basis of the chromatography-solid phase-technology with a cocktail from gold-labelled polyclonal indicator-antibodies from the mouse and biotinylated polyclonal capture-antibodies was developed. The assay system contained at least 0.3 µg of each antibody. 200 µl heparinised whole blood or centrifuged plasma were added to the test device. After separation of the cellular blood components from the plasma fraction through a fibreglass-fleece, the plasma migrating through the fleece was taken up into a buffer, and added to the adsorbed antibodies. The antibodies and the sCD40L-molecules of the samples formed sandwich-complexes that migrated to the signalling zone, and accumulated in the vision panel by means of interaction with biotin-streptavidin. Positive results (sCD40L 4.7 µg/l were indicated by a coloured line that developed within 15 minutes. The indicator antibodies that were unbound migrated further, and were bound at a control line consisting of a solid phase-antimouse-IgG-antibody ($\geq 0.2$ µg). The occurrence of said control line downstream from the signalling line confirmed the accurate test function including the unobstructed flow of the plasma.

7. In Vivo-Activation of Platelets

Blood samples that were anti-coagulated with sodium citrate were immediately treated for 10 minutes with 1.1% paraformaldehyde in PBS, diluted 4.6-fold in distilled water for a lysis of the erythrocytes, and the fixed cells were washed in PBS. In order to determine P-selectin in platelets the resuspended pellet was incubated 60 minutes with phycoerythrine (PE)-conjugated glycoprotein IIb-specific monoclonal antibody (CD41; Dako Carpenteria, California), and fluorescein isothiocyanate (FITC)-conjugated P-selectin-specific monoclonal antibody (BD Pharmingen, San Diego, Calif.). The platelets were characterised by their characteristic forward- and sideward-light scattering, and the binding of the PE-conjugated glycoprotein IIb-specific antibodies. The activation of platelets is expressed in % of the P-selectinpositive platelets. In order to identify circulating monocyte-platelet-aggregates, the cells were stained with FITC-conjugated glycoprotein IIIa-specific monoclonal antibodies (CD61; Dako) and PE-conjugated monoclonal antibodies against CD14 (BD Pharmingen). The monocytes were identified by their characteristic forward- and sideward-light scattering properties and the binding of PE-conjugated CD14-specific antibodies. Monocyte-platelet-aggregates were defined as monocytes in which glycoprotein IIIa could be detected, and were indicated in percent of the total number of monocytes (Michelson A D, Barnard M R, Krueger L A, Valeri C R, Furman M I, Circulation 2001; 104:1533-7). Every staining was incubated in the presence of saturating concentrations of a monoclonal non-conjugated rat-antibody against Fc-receptor (anti-CD16/32, BD Pharmingen) in order to reduce the unspecific binding, and isotypeidentical antibodies served as control ($IgG_1$-PE and $IgG_{2a}$-FITC; BD Pharmingen). In total, 50,000 signals were analysed with the aid of FACS-Calibur (Becton/Dickinson, Heidelberg), and the CellQuest-software (BD Pharmingen).

8. Statistical Methods

The assay results were compared with the data base after a blind evaluation of the biochemical markers and the activation of platelets. In order to be able to distinguish patients with different grades of a cardiac risk, an orientated data analysis was chosen. CAPTURE-patients were grouped according to the sCD40L-concentration of the quintile. A logistic regression analysis was performed for each of the four points in time (24 hours, 72 hours, 30 days, and 6 months), and patients in the first quintile (sCD40L<2.0 µg/l) served as a reference. Receiver operating characteristics (ROC) curve analysis over the dynamic range of the sCD40L-test was used in order to identify the threshold concentrations for sCD40L that provided the highest predictive values for the risk stratification of patients with acute coronary syndromes. The effect of an increase of the biochemical marker on the fate of the patient was evaluated by using a Cox proportional-hazards regression model that included the base line-values of the prognostic factors (e.g. ECG-findings, cardiac risk factors, age and gender), and the randomly selected treatment (Harrell F E, Jr., Lee K L, Pollock B G. J Natl Cancer Inst 1988; 80:1198-202). All results for continuous variables were expressed as medians with 95% confidence interval. In experiments with more than two subgroups, identical intermediate groups were analysed by the T-test (two-sided) or ANOVA. Post hoc-range tests and pair-wise multiple comparisons were performed with the T-test (two-sided) with Bonferroni-adjustment. The comparison of categorical variables was performed with the Pearson-chi$^2$-test. All analyses were performed with SPSS 11,0 (SPSS, Inc.). Values of p<0.05 were regarded as statistically significant.

Example 1a

Association Between Cardiac Risk and sCD40L-Concentration

Figure 1:
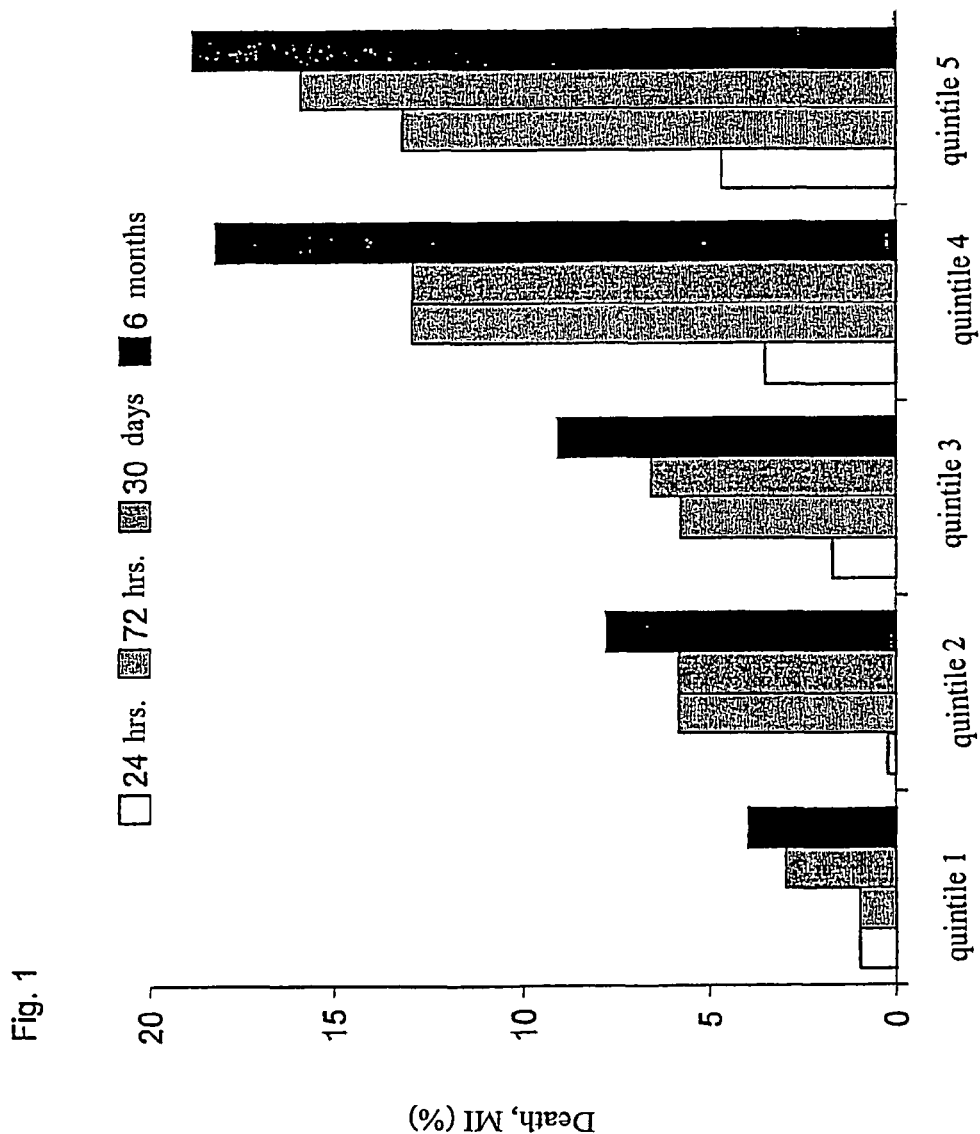

The characteristics of the outcome for the population that was selected for this study (n=1088, 86% of the CAPTURE-patients) did not differ from the total population of the study regarding age, gender, cardiovascular risk profile, and accompanying treatment before and after the random selection. The reduction of cardiac events in the abciximab-group of the population was comparable with the overall CAPTURE-population (before PTCA: 2.2% placebo vs. 0.9% abciximab, p=0.094; after PTCA: 7.9% vs. 3.5%, p=0.002; after 30 days: 9.0% vs. 4.2%, p=0.002) (CAPTURE. Lancet 1997; 349: 1429-35).

sCD40L could be detected in the base line-serum samples of all 1088 patients with an average of 4.5 µg/l (range 0.003-20.4). The sCD40L-concentration did not correlate with the measured concentrations of TnT (r=0.14) and CRP (r=0.11). The patients of the placebo-group (n=544) were grouped into quintiles in accordance with their sCD40L-concentrations as measured: (sCD40L 1)<1.93 µg/l (n=100), (sCD40L 2) 1.93-3.50 µg/l (n=102), (sCD40L 3) 3.50-5.00 µg/l (n=121), (sCD40L 4) 5.00-6.30 µg/l (n=115) or (sCD40L 5)>6.30 µg/l (n=106). During the first 24 hours, the combined endpoints mortality and non-deadly myocardial infarction were slightly elevated only in the fifth sCD40L-quintile compared to the first quintile (p=0.13) (FIG. 1). At later time points (72 hours, 30 days, 6 months), these events occurred significantly more often both in the fourth as well as in the fifth (p=0.003, p=0.0004 or p=0.001).

On the basis of the above described results, the samples of the patients were grouped in accordance with the calculated threshold concentrations. 221 patients (40.6%) exhibited sCD40L-concentrations of 5.0 µg/l or above, and 323 patients exhibited values of <5.0 µg/l. As shown in Table 1, no significant differences occurred in the characteristics of the outcome of both groups. In patients with lower sCD40L-concentrations the combined endpoints lethal and non-lethal myocardial infarction were significantly different from those of patients with elevated sCD40L-concentrations both 24 hours before the method (4.1% vs. 0.9%; p=0.016) as well as 72 hours thereafter (including coronary interventions in all patients) (13.1% vs. 4.3%; vs. 4.3%; p<0.001) (FIG. 2a). During the 6-month follow-up period the curves that indicated the frequency of an event in patients with high or low sCD40L-concentrations (FIG. 2b) diverged further. Significant differences were found both after 30 days (14.5% vs. 5.3%; p<0.001) as well as after 6 months (18.6% vs. 7.1%; p<0.001). Due to the relatively low mortality of the CAPTURE-group, the endpoint mortality after 6 months did not significantly differ between both groups (2.3% vs. 1.5%; p=0.72). The predictive value of sCD40L was independent from a myocardial necrosis. A group of patients with elevated cardiac risk (13.6%) was identified in TnT-negative patients by means of the sCD40L-concentration that did not differ significantly from the cardiac risk of TnT-positive patients (14.0%; p=1.00). Receiver operating characteristics curve analysis confirmed a threshold concentration of 5.0 µg/l for the maximised predictive value of sCD40L. Repeated non-urgent cardiologic interventions during the first 6 months in patients with high sCD40-concentrations were not significantly different from those in patients with lower sCD40L-concentrations (6.2% vs. 4.5%; p=0.45).

Out of 626 patients without ST-elevation that were admitted in the emergency room with acute chest pain, 308 patients suffered from an acute coronary syndrome (117 patients had suffered from an acute myocardial infarction, supported by a troponin-increase 0.1 µg/l). The following diagnosis was made in the other patients: n=91 stable angina, n=10 lung embolism, n=11 congestive heart insufficiency, n=7 myocarditis, and n=199 no evidence for a heart disease. sCD40L-concentrations were significantly higher in patients with acute coronary syndromes (4.53 [3.19-5.87]µg/l) compared to patients with stable angina (2.41 [1.99-3.52] µg/l; p<0.001) or patients without indications of a heart disease (1.57 [0.88-1.76] µg/l; p<0.001). The average value for the upper reference limit (URL) of 97.5 in patients without indications of cardiac disturbances was 4.7 µg/l, and the URL-average value of 99 was found at 6.2 µg/ml. Similarly to the results that were obtained in the CAPTURE-study, the sCD40L-serum concentrations did not correlate with necrosis markers (troponin T), inflammatory markers (CRP, TNF-α), and adhesion molecules (ICAM-1). In patients with acute coronary syndromes, 43.5% exhibited sCD40L-serum concentrations above the 97.5 URL-average value, and 21.8% exhibited sCD40L-serum concentrations above des 99 URL-average value. By using a defined threshold concentration for sCD40L of 5.0 µg/l, patients with an elevated sCD40L-serum concentration were identified as a high-risk-population (defined risk quotient 3.00 [1.35-6.71]; p=0.009). Inside the overall heterogenic population of patients with chest pain, the defined threshold concentration of 5.0 µg/l was also reliable in identifying patients that exhibited a profound risk for cardiologic events during the following 30 days (defined risk quotient 6.65 [3.18 to 13.89]; p<0.001). The area under the ROC-curve was 0.75 [0.67-0.83], and a maximised predictive value was reached at a threshold concentration of 4.8 µg/l.

Example 2a

Angiographic Results and sCD40L-Concentration

The base line coronary angiograms in patients with elevated sCD40L-concentrations showed more complex characteristics of the lesions. Lesions of type B2+ or C were documented in 40.6% of the patients with high sCD40L-concentrations, whereas only 27.5% of the patients with low sCD40L-concentrations exhibited more complex characteristics of the lesions (p=0.004).

In 59.6% of the patients with high sCD40L-concentrations and in 58.9% of the patients with low sCD40L-concentrations the base line value for the TIMI-flow-through was normal (p=0.049). For 7.8% of the patients with high sCD40L-concentrations a TIMI-flow-through=1 was documented compared to 5.7% of the patients with low sCD40L-concentrations (p=0.67).

A thrombus at the time of presentation was visible in 11.1% of the patients with high sCD40L-concentrations compared to 4.8% patients with low sCD40L-concentrations (p=0.009). All patients with visible thrombus formation exhibited sCD40L-concentrations of >2.5 µg/l.

Example 3a

Effect of Abciximab on the sCD40L-Concentration

Figure 3:
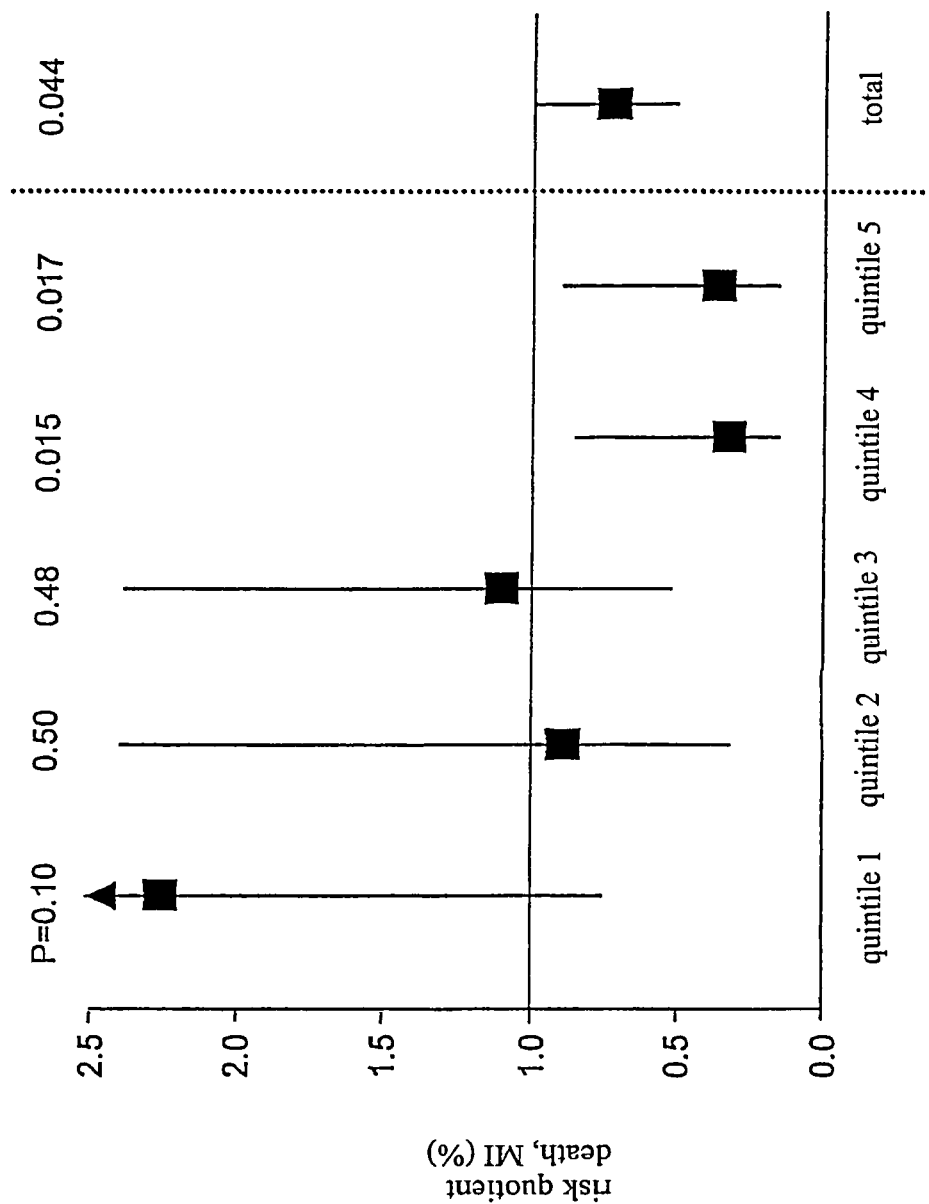

A logistic regression analysis pointed towards a significant association between the effectiveness of a treatment with abciximab and the sCD40L-concentrations (p<0.001). The patients were grouped into quintiles as noted above. For the first two quintiles, no differences were observed with respect to a cardiac risk at treatment with placebo or abciximab (FIG. 3). A significant and comparably pronounced reduction of cardiac events was documented for the upper two quintiles. The finding of a change of the disparity to 0.35 between the second and the quintiles suggests a favourable threshold concentration of the sCD40L-concentrations in this range. Accordingly, the curves that show the frequency of a cardiac event in form of a lethal or non-lethal myocardial infarction were generated by using a threshold concentration of 5.0 µg/l. Events before these methods were rare in patients with low sCD40L-concentrations that received placebo (0.9%), whereas in 3.4% of the patients events occurred in association with a coronary intervention (FIG. 4a). In patients with low sCD40L-concentrations no difference was observed between patients that received abciximab and those that received placebo (24 hours: 1.2% vs. 0.9%; 72 hours: 3.8% vs. 4.3%). In the following 6 months, only very few additional events were registered. The overall frequency was 7.1% (FIG. 4b).

In contrast to this, the frequency of attacks was significantly higher in patients with high sCD40L-concentrations receiving placebo, both before PTCA (4.1%) as well as under PTCA (9.0%) as well as in the following time after discharge, leading to an overall frequency of 18.6% after six months. Events that occurred before and under PTCA were effectively reduced to 0.5% before PTCA (risk quotient 0.12 [0.01-0.92]; p=0.013), and 2.9% for PTCA-related events (risk quotient 0.19 [0.08-0.49]; p<0.001) by a treatment with abciximab. This improvement was maintained for six months after the event, leading to a cumulative frequency of the events of 7.8% vs. 18.6% in the placebo group (risk quotient 0.37 [0.20-0.68]; p=0.001). This value is comparable with the one that was observed in patients with low sCD40L-concentrations (7.1%). Furthermore, the effect of the glycoprotein IIb/IIIa-inhibition without the occurrence of a myocardial necrosis was obvious. In TnT-negative patients, a subgroup of patients was identified by means of the sCD40L-concentration that exhibited a significant reduction of cardiac events when they received abciximab (2.8% vs. 10.2%; placebo vs. abciximab; p=0.022).

The dissolution of a thrombus during the ordered treatment before coronary intervention was particularly noticeable in patients with high sCD40L-concentrations when treated with abciximab, with a relative reduction of 63% (placebo: −21%; p<0.01). A thrombus formation in patients with low sCD40L-concentrations was rare and a significant dissolution was neither achieved in the placebo group (p=0.75) nor in the abciximab-group (p=0.82).

Example 4a sCD40L as Marker of an Activation of Platelets In Vivo

Figure 5:
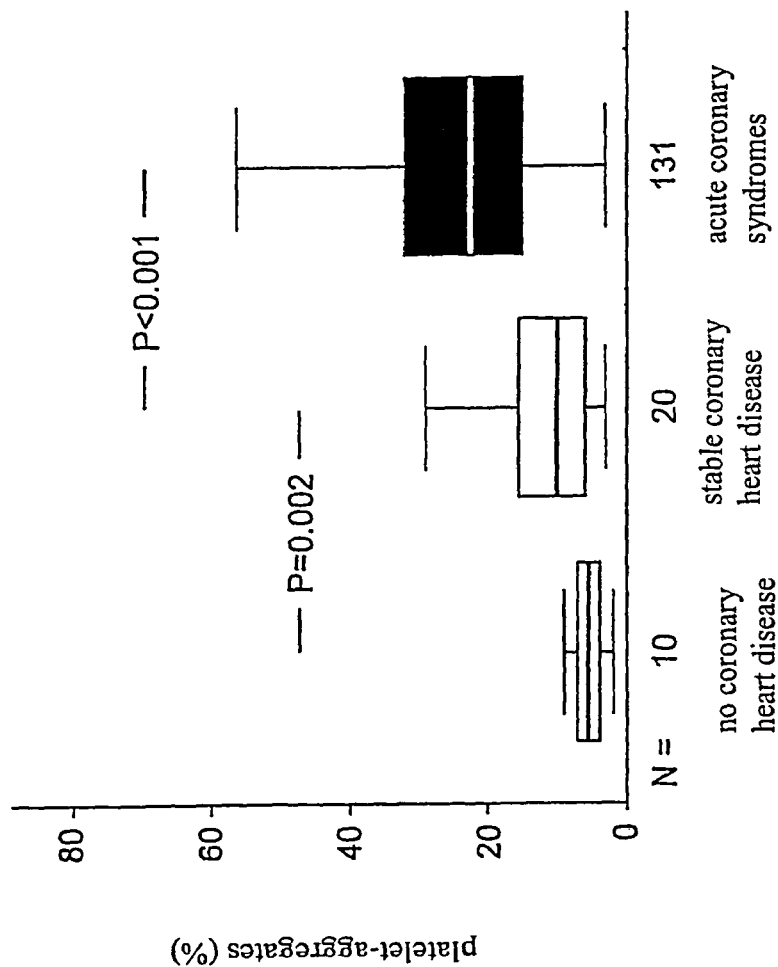
Figure 6:
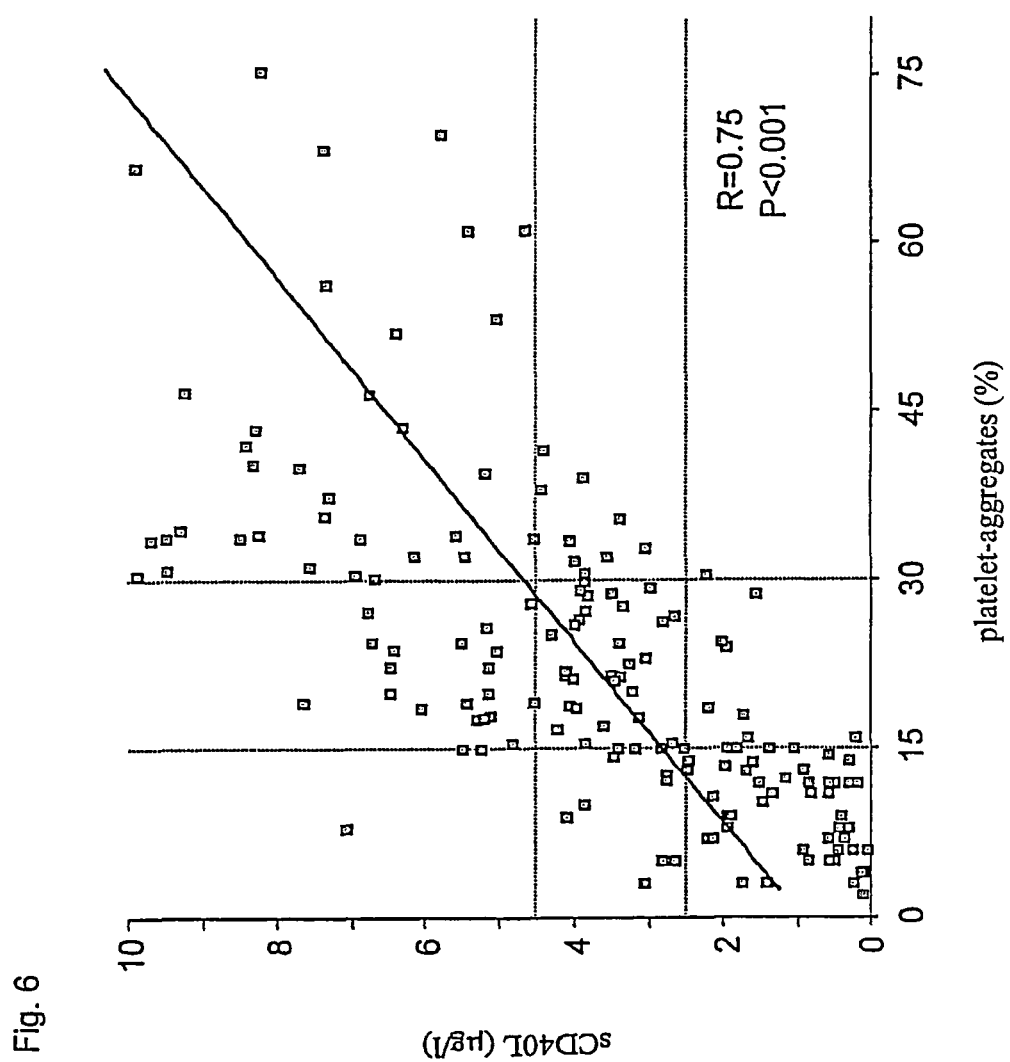
FIG. 6 shows that the sCD40L-serum concentrations do strictly correlate with the extent of the activation of platelets in patients with and without acute coronary syndromes. The interrupted lines divide the patients into tertiles according to the activation of platelets (<15%, 15%-30%, >30%) or sCD40L-serum concentrations (<2.5 g/l; 2.5-4.5 µg/l; >4.5 µg/l).

In order to verify the hypothesis that sCD40L indeed constitutes a marker for the activation of platelets, the ratio of the activation of platelets and the sCD40L-serum concentrations was prospectively analysed in a subgroup of patients with acute chest pain (n=151). The extent of the activation of platelets in patients with acute coronary syndromes was significantly elevated compared both to patients with stable coronary heart disease as well as to patients without coronary heart disease (FIG. 5). A strict correlation between the activation of platelets as determined by means of monocyte-platelet-aggregates (%) and the sCD40L-concentration was observed (r=0.75; p<0.0001) (FIG. 6). Similar results were obtained for P-selectin (p<0.001). The patients were grouped into tertiles according to their measured sCD40L-concentrations: (sCD40L1)<2.5 µg/l (n=55), (sCD40L 2) 2.5-4.5 µg/l (n=50), and (sCD40L 3)>4.5 (n=56), respectively. In patients of the first sCD40L-tertile, the percentage of monocyte-platelet-aggregates was 11.3% [9.6-12.9]. In the second and third sCD40L-tertiles the activation of platelets was significantly higher (22.3 [19.8-24.8]%, and 34.1 [30.0-38.3]%; p<0.001, respectively). It is particularly interesting that in all patients (with the exclusion of one patient) that exhibited sCD40L-serum concentrations of >4.5 µg/l, at least 15% of the monocytes were aggregated with platelets, indicating a pronounced activation of platelets in these patients. In contrast thereto the serum concentrations of soluble P-selectin showed a markedly less pronounced association with the activation of platelets (r=0.41 for monocyte-platelet-aggregates, and r=0.36 for P-selectin, respectively). It could be found in a multi-variance-regression analysis that a diabetes-disease (p=0.015), a hypercholesterolemia (p=0.006), and the sCD40L-concentration (p<0.0001), but not the concentration of soluble P-selectin, was significantly associated with the activation of platelets (monocyte-platelet-aggregates>30%).

TABLE 1

Base line characteristics of sCD40L in the placebo group

| | sCD40L low | sCD40L high |
|---|---|---|
| n | 323 | 221 |
| Male | 73.3% | 70.2% |
| Age | 60.5 ± 9.9 | 62.3 ± 10.5 |
| Anamnesis | | |
| Angina for more than 4 weeks | 57.5% | 54.6% |
| infarction 14-30 days | 3.5% | 2.4% |
| infarction more than 30 days | 19.5% | 21.0% |
| PTCA | 19.1% | 15.9% |
| CABG | 3.5% | 3.4% |
| Risk factors | | |
| Diabetes | 12.1% | 9.6% |
| Hypercholesterolemia | 32.5% | 33.6% |
| Hypertension | 39.3% | 34.5% |
| Smoker | 40.9% | 42.1% |
| Medication before registration | | |
| Aspirin | 98.1% | 97.7% |
| Heparin i.v. | 99.2% | 98.6% |
| Nitrate i.v. | 98.8% | 99.7% |
| Beta-blocker | 65.0% | 61.4% |
| $Ca^{2+}$-antagonists | 56.0% | 55.2% |

TABLE 2

Lethal and non-lethal myocardial infarction within the first 6 months (multi-variance-regression analysis)

| Variable | OR | 95% CI | p-value |
|---|---|---|---|
| Gender | 0.91 | 0.68-1.39 | 0.16 |
| Age higher than 65 years | 1.36 | 0.91-1.82 | 0.34 |
| Diabetes mellitus | 1.22 | 0.83-1.49 | 0.61 |
| Hypercholesterolemia | 0.90 | 0.68-1.13 | 0.59 |
| Hypertension | 1.00 | 0.89-1.04 | 1.00 |

TABLE 2-continued

Lethal and non-lethal myocardial infarction within the first 6 months (multi-variance-regression analysis)

| Variable | OR | 95% CI | p-value |
|---|---|---|---|
| History of a CHD | 0.86 | 0.65-1.19 | 0.72 |
| ST-depression | 1.04 | 0.76-1.54 | 0.74 |
| TnT > 0.1 µg/l | 2.94 | 1.75-7.26 | <0.001 |
| CRP > 10 mg/l | 2.03 | 1.11-3.59 | 0.018 |
| sCD40L > 5.0 µg/l | 2.71 | 1.51-5.35 | 0.001 |

II. PlGF

PlGF was initially identified in the placenta and stimulates vascular smooth muscle growth, recruits macrophages in arteriosclerotic lesions, up-regulates the production of TNF-α, and MCP-1 by macrophages, and stimulates the pathological angiogenesis. Much more important, it was experimentally shown from the inhibition of the effects of PlGF by blocking its receptor tyrosine kinase Flt-1, that this represses both the growth of arteriosclerotic plaques as well as the vulnerability by the inhibition of the inflammatory infiltration of cells. These data suggest that PlGF might serves as a primary inflammatory indicator of the instability of arteriosclerotic plaques.

Thus, the prognostic significance of PlGF in patients with acute coronary syndromes was employed by using the data of the patients with acute coronary syndromes that were included in the CAPTURE study (c7E3 "Anti Platelet Therapy in Unstable Refractory angina"), and the diagnostic and the prognostic significance was then preliminary validated in a large population of patients that were admitted with pain in the chest. The PlGF serum levels were measured in 1088 patients from the CAPTURE study with acute coronary syndromes. Furthermore, the diagnostic and prognostic significance of PlGF serum levels was preliminary validated in a heterogeneous group of 619 patients with acute pain in the chest. The incidence of myocardial infarction with lethal or non-lethal outcome was recorded during the follow-up period.

1. Patients

Design of the sets of patients with acute coronary syndromes. The CAPTURE-study registered 1265 patients with acute coronary syndromes (61% male, in the age of 61±10 years). All CAPTURE-patients were complaining about reoccurring chest pain in the resting state, associated with ECG-modifications during a treatment with intravenous heparin and glycerol trinitrate. The overall patient-population was subjected to a coronary angiography before the randomisation which significantly indicated the occurrence of a markedly coronary arterial disease with triggering lesions of >70% that were suitable for the angioplasty. Heparin was applied starting before the randomisation to at least 1 h after the PTCA procedure. Coronary interventions were scheduled in all patients within 18 to 24 hours after the start of the treatment. The patients were randomly assigned to a treatment by abciximab or placebo. Primary endpoints of the study were mortality and non-fatal myocardial infarction during the 6-months follow-up-period. Serum samples were taken 8.7 [75% CI 3.6-11.3] hours after onset of the symptoms.

2. Validation of Patients with Acute Chest Pain

A separate group of 626 patients with chest pain (161 women and 465 men, average age 61 [38-82] years) that were presented in the emergency room in a consecutive row with acute chest pain that lasted for less than 12 hours (average 5.1 [2.1-10.4] hours) was established as a set. Patients with a characteristic ST-elevation in the base-ECG or a documented acute myocardial infarction during the preceding 2 weeks were not taken into account. Serum samples were obtained at the time of admission (before the start of treatment), and 4 hours later, kept on ice, centrifuged within 20 minutes after sample collection, and stored at −80° C. for later analysis. The patients were observed until discharge from the hospital and 30 days thereafter, in order to register lethal and non-lethal myocardial infarctions. The presence of a coronary arterial disease was detected by one of the following criteria: ECG-indications of a myocardial ischemia (novel changes in the ST-stretch or inversion of the T-wave), a coronary heart disease in the anamnesis (myocardial infarction or coronary revascularisation, a positive stress test or restriction of the diameter of a main coronary artery by at least 50% in an early angiogram). Patients without coronary heart disease had to show a normal coronary angiogram.

Primary endpoints of the study were mortality, myocardial infarction or the necessity for immediate intervention (angioplasty, bypass-operations of the coronary artery) due to an instability during 30 days or 6 months. In patients that suffered from a heart attack during the period in the hospital, this was accordingly diagnosed, if their values of the enzymatic activity of the creatine kinase in at least two samples was more than three times as high than the upper limit of the normal range, or if their ECG exhibited novel distinct Q-waves in more than two subsequent intervals. This strict definition was chosen in order to exclude any unimportant small increase of the creatine kinase after PTCA. In patients with a myocardial infarction after discharge, this was defined accordingly, if their values of the enzymatic activity of the creatine kinase were more than twice as high than the upper limit of the normal range, or if their ECG exhibited novel distinct Q-waves in two or more subsequent intervals. The secondary endpoint was the symptomatic coronary restenosis of the treated lesion with a diameter of the stenosis of 70%, and the necessity for a repeated revascularisation during the subsequent 6 months.

3. Biochemical Analysis

Serum samples were centrally stored at −80° C. The determinations of the cardiac markers were performed in the research laboratory of the university Frankfurt without knowledge of the disease history of the patient and the treatment as ordered. The serum levels of PlGF and VEGF were measured by means of ELISA (R&D Systems, Wiesbaden). For a quantification of cardiac troponin T (TnT), a one-step enzyme-immunoassay on the basis of the electrochemiluminescence technology (Elecsys 2010, Roche Diagnostics) was used. Highly sensitive C-reactive protein (hsCRP) was measured with the aid of the Behring BN II nephelometer (Behring Diagnostics). A diagnostic threshold value of 10.0 mg/l was used [9, 18].

4. Quantitative Determination of PlGF

The PlGF-concentration was determined by using the sandwich-enzyme-immunoassay-technology (R&D Systems, Wiesbaden). A microtitre plate was coated with a polyclonal antibody that was specifically directed against PlGF. Standards and samples were pipetted into the wells, and present PlGF was bound by the immobilised antibody. After unbound material was washed away, an enzyme-coupled polyclonal antibody which was specifically directed against PlGF was added to the wells. After a washing step in order to remove unbound antibody-enzyme-reagent a substrate-solution was added to the wells, and the colour developed in relation to the amount of PlGF that was bound in the first step. The development of colour was stopped, and the intensity of the colour was measured.

5. Statistical Methods

The assay results were compared with the data base after a blind evaluation of the biochemical markers. In order to be able to distinguish patients with different grades of a cardiac risk, an orientated data analysis was chosen. The Cox proportional-hazards regression model was used in order to estimate the relative risk for cardiovascular events, and the patients were grouped according to the PlGF-concentration of the quintiles. The post-hoc analysis of the quintiles was performed by using the Cox proportional-hazards regression model with the PlGF quintiles as a categorical variable, and patients in the first quintile served as a reference. Receiver operating characteristics (ROC) curve analysis over the dynamic range of the PlGF-assay was used in order to identify the threshold concentration for PlGF that provided the highest predictive value for the risk stratification of patients with acute coronary syndromes. The effect of the baseline characteristics (whereby p=0.10 was required in order to include a variable into the model) and other biochemical markers on any associations between PlGF levels and cardiovascular events as observed was performed by using stepwise Cox proportional-hazards regression model. All results of the continuous variables are expressed as median±standard deviation. The comparison between the groups was analysed by a t-test (two-sided). The comparison of categorical variables was generated by the Pearson $\chi^2$ test. p-values of <0.05 were regarded as statistically significant. All analyses were performed with SPSS 11.0 (SPSS Inc., Chicago).

Example 1b

Association Between Cardiac Risk and PlGF-Concentration

The characteristics of the outcome for the population that was selected for this study (n=1088, 86% of the CAPTURE-patients) did not differ from the total population of the study in view of age, gender, cardiovascular risk profile, and accompanying treatment before and after the random selection. The reduction of cardiac events in the abciximab-group of the population was comparable with the overall CAPTURE-population, both before PTCA (2.2% placebo versus 0.9% abciximab; p=0.07), as well as after PTCA (7.9% versus 3.5%; p=0.001), and at 30 days (9.0% versus 4.2%; p=0.001).

Figure 7:
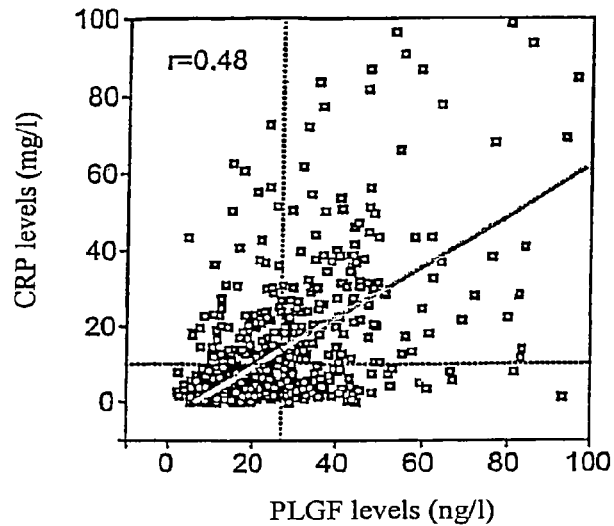
FIG. 7 shows the association between PlGF and hsCRP as a downstream acute-phase reactant (n=1088).
Figure 8:
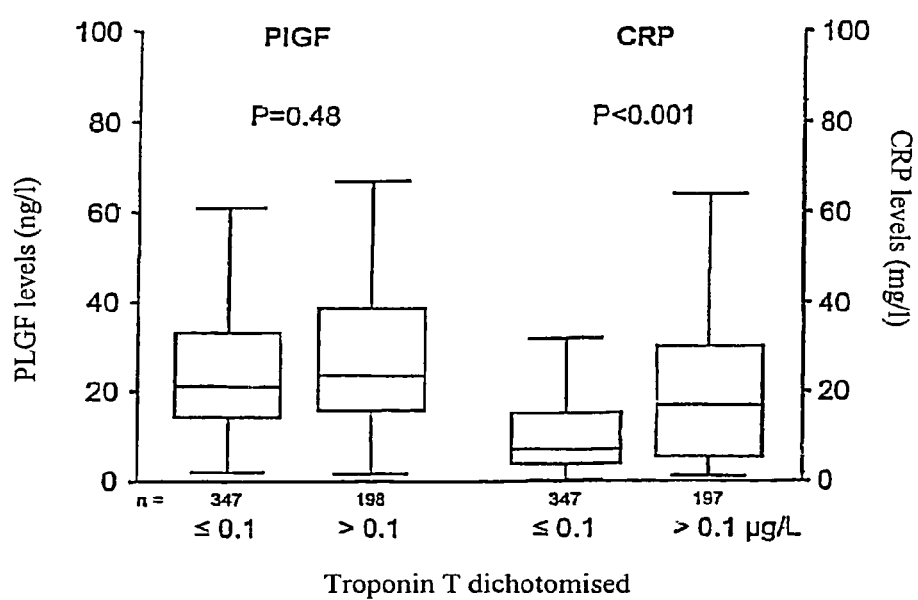
FIG. 8 shows each of the PlGF and hsCRP serum levels according to the base-line troponin T status (n=1088).

PlGF could be detected in the base line-serum samples of 95.6% of the patients of the study with an average of 23.0 ng/l (range 7.0-181.2). The PlGF serum level did not correlate with the measured concentrations of troponin T (r=0.14) and VEGF levels (r=0.07), but exhibited a significant correlation with hsCRP serum level (r=0.48) (FIG. 7). The PlGF serum level did not differ between troponin T-positive and troponin T-negative patients, whereas the hsCRP serum levels were significantly higher in troponin T-positive patients (FIG. 8). The patients of the placebo-group (n=547) were grouped into quintiles according to their measured PlGF serum levels: (PlGF 1)<13.3 ng/ln=109), (PlGF 2) 13.4-19.2 ng/l (n=110), (PlGF 3) 19.3-27.3 ng/l (n=110), (PlGF 4) 27.3-40.0 ng/L (n=109), and (PlGF 5)>40.0 ng/l (n=109), respectively. During the first 24 hours the combined endpoints mortality and non-lethal myocardial infarction were not different between the PlGF-quintiles (p=0.11) (FIG. 9). At later points in time (72 hours, 30 days, 6 months) the event-rates showed significant differences between the PlGF quintiles. At 72 hours follow-up examination the event-rates were significantly higher in the fourth and fifth quintile when compared with the first quintile (p=0.038 and p=0.011, respectively). During the subsequent 6 months follow-up examination, the event-rates diverged further, leading to significant differences for the fourth and fifth quintile at 30 days (p=0.005 and p=0.017, respectively), and 6 months follow-up examination (p=0.002 and p=0.001, respectively).

Figure 11A:
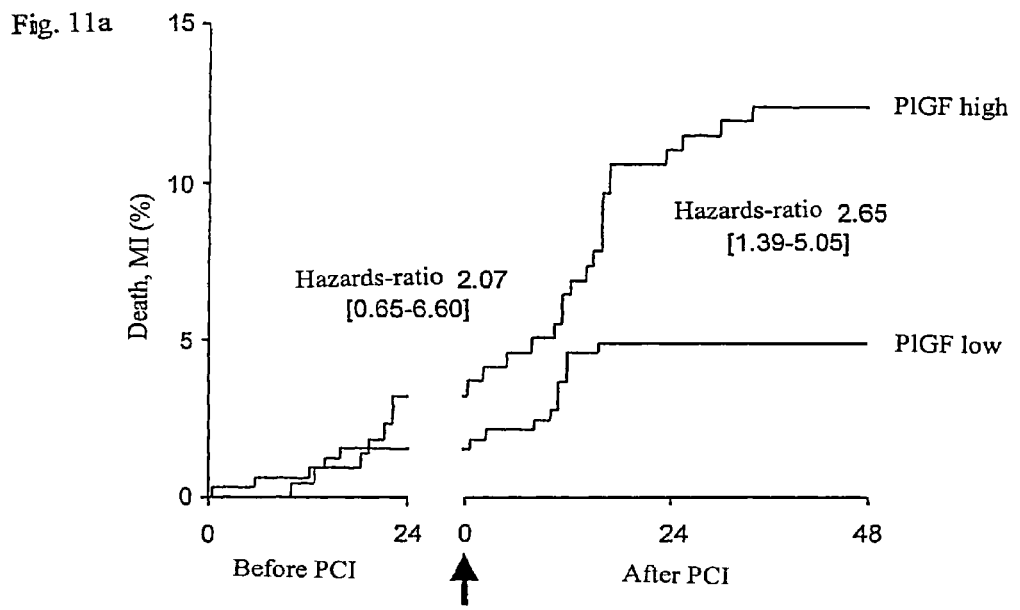
Figure 11B:
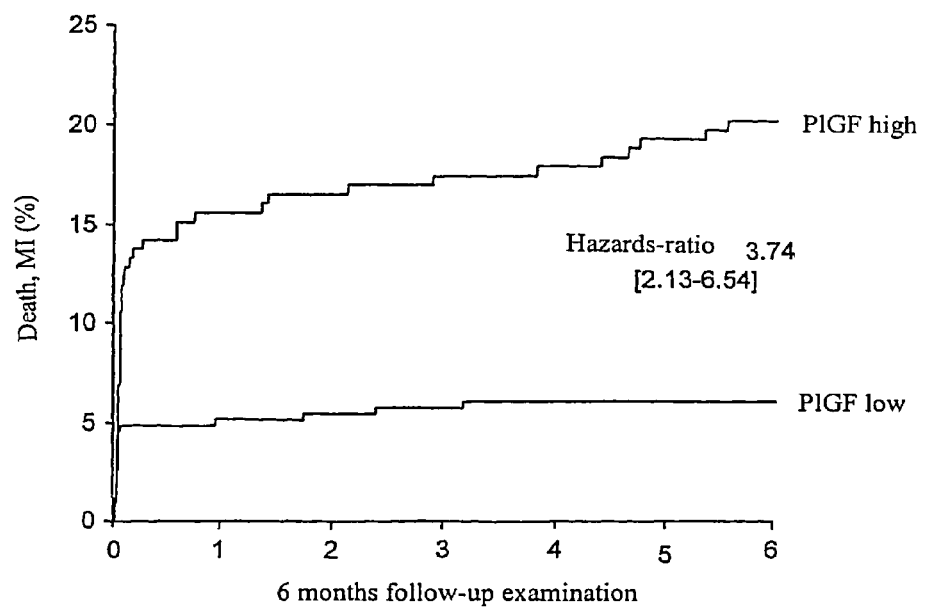
Figure 12A:
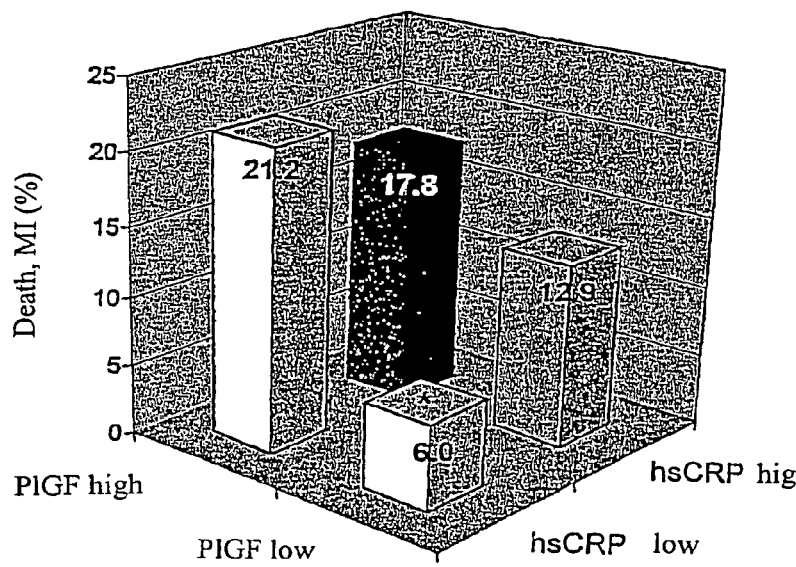

Receiver operating characteristics curve analysis confirmed a threshold value of 27.0 ng/l for the maximised predictive value of PlGF (FIG. 10). On the basis of this threshold value, 223 patients (40.8%) had PlGF serum levels above or identical to 27.0 ng/l, and 324 patients below 27.0 ng/l. As shown in Table 3 small differences in the outcome characteristics of both groups occurred. Patients with elevated PlGF serum levels more often were diabetics and had hypertension and exhibited significantly higher hsCRP serum levels (Table 3). In patients with high PlGF serum level, the combined endpoints lethal or non-lethal myocardial infarction were significant different from patients with low PlGF serum levels. After 72 hours (including coronary intervention in all patients) 12.1% of the patients with high PlGF serum levels experienced a negative event, compared to 4.9% for patients with low PlGF serum level (p=0.002) (FIG. 11a). During the 6-month follow-up period the curves indicating the frequency of an event diverged further between patients with high or low PlGF serum levels (FIG. 11b). Significant differences were found both after 30 days (15.8% versus 3.6%; p=0.001) as well as after 6 months (20.3% versus 4.9%; p<0.001). Despite the relatively low mortality of the CAPTURE-group the endpoint-mortality between both groups (4.0% versus 0.9%; p=0.021) differed significantly after 6 months. In a multivariate analysis that included the baseline characteristics and biochemical markers (troponin T, VEGF, hsCRP), PlGF remained as an independently effective predictor of elevated cardiac risk both at 30 days follow-up examination (adjusted hazards-ratio 3.34 [95% CI 1.79-6.24]; p<0.001), and at 6 months follow-up examination (adjusted hazards-ratio 3.58 [95% CI 1.48-7.72]; p<0.001) (Table 4). A separation of the patients into four groups based on their PlGF and hsCRP levels showed that PlGF identified a subgroup of patients with low hsCRP serum levels that suffered from a significantly elevated cardiac risk. Patients with low hsCRP serum levels but PlGF serum levels above 27.0 ng/l had a significantly higher risk compared to patients that exhibited low levels for both hsCRP and PlGF (23.6% versus 3.9%; p=0.001) (FIG. 12a).

Figure 12B:
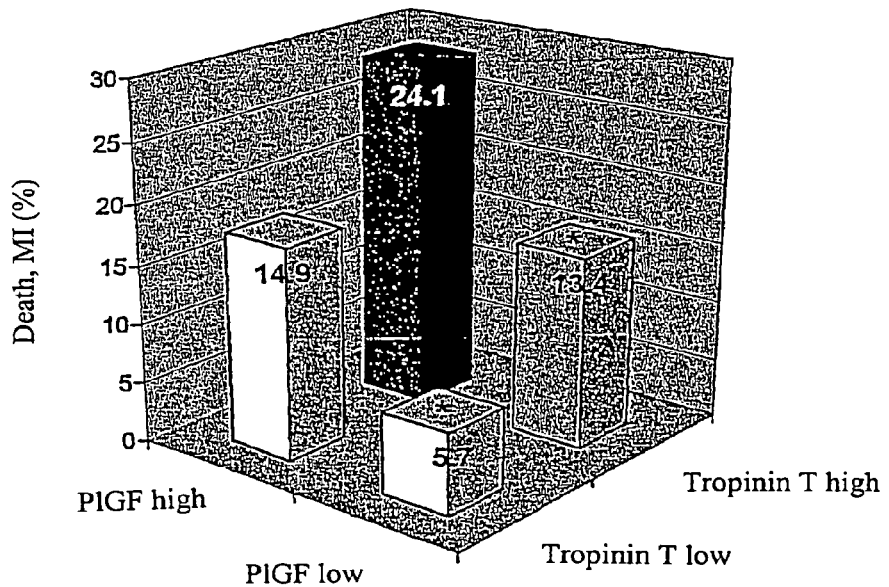

Furthermore, the predictive value of PlGF was independent from myocardial necrosis. High PlGF serum levels showed an elevated cardiac risk both in troponin T-positive patients (15.4% versus 4.1%; P=0.005) as well as in troponin T-negative patients (26.1% versus 10.1%; p=0.001) (FIG. 12b).

Example 2b

Effect of Abciximab in View of the PlGF-Serum Level

A logistic regression analysis pointed towards a border-line-significant connection between the effectiveness of a treatment with abciximab and the PlGF-concentrations (p=0.043). Patients with elevated PlGF serum levels that received abciximab had a significantly lower risk at 30 days follow-up examination (adjusted hazards-ratio 0.38 [0.19-0.74]; p=0.005). This significant difference was maintained at 6 months follow-up examination (0.57 [0.34-0.96]; p=0.037). In contrast to this, patients with low PlGF serum levels did not gain a significant therapeutic benefit from a treatment with abciximab (30 days follow-up examination:adjusted hazards-ratio 0.59 [0.27-1.33]; p=0.23).

Example 3b

Discharge PlGF Serum Level are Predictive for the Long-Term Outcome

A second blood sample that was taken before discharge (7.2±4.5 days following randomisation) could be obtained for 489 patients of the 547 placebo-patients (89.4%). The PlGF serum levels decreased from an average of 27.12±19.56 ng/l at baseline to 23.4±26.2 ng/l at discharge (p=0.012). For patients with a PlGF serum level at discharge of above 27.0 ng/l, the occurrence of mortality and non-fatal myocardial infarction was significantly higher when compared to patients having low PlGF serum levels, both at 30 days (4.6% versus 0.8%; p=0.019) and 6 months follow-up examination (7.4% versus 2.2%; p=0.005) (FIG. 13).

Example 4b

Validation of the PlGF-Threshold Values in Patients with Acute Chest Pain

Out of 626 patients with acute chest pain, 308 patients suffered from an acute coronary syndrome (117 patients had a non-ST-elevated myocardial infarction). The other patients were grouped according to the following diagnoses: n=91 stable angina, n=10 pulmonary embolism, n=11 congestive heart failure, n=7 myocarditis, and n=199 no indications for a heart disease. The PlGF serum level were significantly increased in patients with acute coronary syndromes (average 28.3 [95% CI 21.3-2.2] ng/l) when compared each to patients with stable angina (average 16.2 [95% CI 13.8-18.6 ng/l; p=0.001), and patients without indications for a heart disease (average 9.6 [95% CI 10.4-12.9 ng/l; p=0.001). The PlGF serum levels in patients with non-ST-elevated myocardial infarction did not differ significantly from PlGF serum levels in patients with unstable angina (30.5 [95% CI 26.9-34.1] versus 28.3 [95% CI 21.3-32.2] ng/l; p=0.42). The 97.5 percent upper reference limit in patients without indications for a heart disease was 24.9 ng/l and the 99 percent upper reference limit was 27.3 ng/l. The PlGF serum level did not correlate with markers of necrosis (troponin T [r=0.07]), but correlated significantly with inflammatory markers (C-reactive protein [r=0.43]).

In patients with acute coronary syndromes, 44.8% of the patients exhibited PlGF serum level above the 99 percent upper reference limit. By using the threshold values for PlGF of 27.0 ng/l patients with elevated PlGF serum level were underlying a significantly higher risk for death and myocardial infarction (adjusted hazards-ratio 2.97 [95% CI 1.74 to 9.06; p=0.014). Within the overall heterogeneous population of patients with chest pain the threshold value of 27.0 ng/l also reliably identified patients that were subject to the highest risk for death and myocardial infarction (adjusted hazards-ratio 4.95 [95% CI 2.50 to 9.79; P 0.001).

Summary of the Examples 1b to 4b

In patients with ACS, PlGF does not correlate with VEGF, troponin T, and ST-segment modifications, but exhibited a significant correlation with hsCRP (p=0.001). Patients with elevated PlGF serum level (>27.0 ng/l; 40.8%) experienced a drastically elevated cardiac risk (death and non-fatale myocardial infarction) both at 30 days (adjusted hazards-ratio 3.34 [95% CI 1.79-6.24]; p=0.001), and at 6 months (adjusted hazards-ratio 3.58 [95% CI 1.48-7.72]; p=0.001) after ACS. The PlGF serum levels were specifically informative in patients with low hsCRP levels. The preliminary validation in patients with acute chest pain led to the result that PlGF serum levels>27 ng/l reliably identified those patients being subject to the highest risk for death and myocardial infarction (adjusted hazards-ratio 4.95 [95% CI 2.50 to 9.79; p=0.001). The elevated risk in patients with higher PlGF serum levels was reduced by the treatment with the glycoprotein receptor inhibitor abciximab (adjusted hazards-ratio 0.38 [0.19-0.74]; p=0.005).

TABLE 3

Base line characteristics according to the PlGF status for the placebo group of the CAPTURE study (n = 547)

|  | PlGF low | PlGF high | p-value |
| --- | --- | --- | --- |
| n | 324 | 223 |  |
| Male | 71.4% | 69.2% | 0.34 |
| Age | 61.4 ± 10.5 | 62.3 ± 10.5 | 0.32 |
| troponin T ≥ 0.1 µg/l | 33.8% | 40.4% | 0.12 |
| CRP ≥ 10.0 µg/l | 29.1% | 67.7% | <0.001 |
| ST-segment depression | 46.0% | 52.1% | 0.18 |
| T-wave inversion | 51.4% | 52.1% | 0.93 |
| History of |  |  |  |
| angina > 4 weeks | 55.3% | 57.4% | 0.64 |
| infarction < 30 days | 12.5% | 13.6% | 0.84 |
| infarction > 30 days | 20.3% | 20.4% | 0.97 |
| PTCA | 16.5% | 18.4% | 0.56 |
| CABG | 3.2% | 3.7% | 0.88 |
| Risk factors |  |  |  |
| Diabetes | 8.2% | 12.5% | 0.034 |
| Hypertension | 33.4% | 39.9% | 0.019 |
| Acute smoker | 39.6% | 41.8% | 0.48 |
| Medication before registration |  |  |  |
| Aspirin | 97.9% | 98.1% | 1.00 |
| Heparin i.v. | 99.0% | 98.9% | 0.98 |
| Nitrates i.v. | 99.4% | 99.3% | 1.00 |
| Beta-blockers | 63.5% | 62.9% | 0.91 |

TABLE 4

Multivariate Cox proportional-hazards-regression model for lethal and non-lethal myocardial infarction within the first 6 months of follow-up examination, derived from the placebo group of the CAPTURE study

| Variable | adjusted hazards-ratio | 95% CI | p-value |
| --- | --- | --- | --- |
| Gender | 0.95 | 0.72 to 1.68 | 0.38 |
| Age > 65 years | 1.22 | 0.65 to 1.47 | 0.50 |
| Diabetes mellitus | 1.22 | 0.83 to 1.49 | 0.61 |
| Hypercholesterolemia | 0.90 | 0.68 to 1.13 | 0.59 |
| Acute smoker | 0.66 | 0.42 to 1.25 | 0.18 |
| Hypertension | 1.04 | 0.91 to 1.25 | 0.95 |
| History of a coronary revascularisation | 0.86 | 0.65 to 1.19 | 0.72 |
| ST-depression | 0.96 | 0.55 to 1.42 | 0.81 |
| hsCRP > 10.0 mg/l | 0.95 | 0.62 to 1.57 | 0.88 |
| troponin T > 0.1 µg/l | 1.76 | 0.98 to 3.46 | 0.084 |
| VEGF > 300 ng/l | 2.16 | 1.05 to 4.11 | 0.031 |
| PlGF > 27.0 ng/l | 3.58 | 1.48 to 7.72 | <0.001 |

III. PAPP-A and Combinations

The prognostic significance of PAPP-A in patients with acute coronary syndromes was employed by using the data of the patients with acute coronary syndromes that were included in the CAPTURE study (c7E3 "Anti Platelet Therapy in Unstable Refractory angina"), and the diagnostic and prognostic significance in a large population of patients that were admitted with pain in the chest was then preliminary validated. The PAPP-A serum levels were measured in patients with acute coronary syndromes from the CAPTURE study. The incidence of myocardial infarction with lethal or non-lethal outcome was recorded during the follow-up period.

1. Patients

Design of the sets of patients with acute coronary syndromes. The CAPTURE-study registered 1265 patients with acute coronary syndromes (61% male, in the age of 61±10 years). All CAPTURE-patients were complaining about reoccurring chest pain in the resting state, associated with ECG-modifications during a treatment with intravenous heparin and glycerol trinitrate. The overall patient-population was subjected to a coronary angiography before the randomisation, which significantly indicated the occurrence of a markedly coronary arterial disease with triggering lesions of >70% that were suitable for the angioplasty. Heparin was applied starting before the randomisation to at least 1 h after the PTCA procedure. Coronary interventions were scheduled in all patients within 18 to 24 hours after the onset of the treatment. The patients were randomly assigned to a treatment by abciximab or placebo. Primary endpoints of the study were mortality and non-fatal myocardial infarction during the 6-months follow-up-period. Myocardial infarction during the stay in hospital including the angioplasty methods were defined by values of the CK enzymatic activity of more than threefold the upper limit of normal in at least two samples, and/or new significant Q-waves in two or more continuous leads. Myocardial infarction after discharge was defined as values of the CK enzymatic activity of more than twofold the upper limit of normal in at least two samples, and/or new significant Q-waves in two or more continuous leads. Since it was shown for other markers, such as, for example, troponin T (TnT) and soluble CD40 ligand (sCD40L) that these interfere with the treatment effect of the glycoprotein IIb/IIIa receptor antagonist abciximab the present analysis was limited to placebo patients with available blood samples (n=547; 86% of the placebo patients). Blood samples were collected 8.7±4.9 hours after outbreak of the symptoms.

2. Biochemical Analysis

Serum samples were centrally stored at −80° C. The determinations of the cardiac markers were performed in the research laboratory of the university Frankfurt without knowledge of the diseases history of the patient and the treatment as ordered. The serum levels of PlGF and VEGF were measured by means of ELISA (R&D Systems, Wiesbaden). For a quantification of cardiac troponin T (TnT), a one-step enzyme-immunoassay on the basis of the electrochemiluminescence technology (Elecsys 2010, Roche Diagnostics) was used. Highly sensitive C-reactive protein (hsCRP) was measured with the aid of the Behring BN II nephelometer (Behring Diagnostics). A diagnostic threshold value of 10.0 mg/l was used. Highly sensitive interleukin-10 (IL-10), vascular endothelial growth factor (VEGF), and sCD40L were measured by means of ELISA (both R&D Systems, Wiesbaden, Germany). We used the following, earlier established diagnostic threshold values: 5.0 μg/l for sCD40L, 300 ng/l for VEGF, 3.5 ng/l for IL-10. Cardiac PAPP-A was determined by using a one-step enzyme-immunoassay on the basis of the electro-chemiluminescence technology (Elecsys 2010, Roche Diagnostics, Mannheim, Germany). By using internal controls, the overall inaccuracy for PAPP-A over the 8-week period was 8.5%.

3. Statistical Methods

The patients were grouped according to the PAPP-A plasma concentrations of the quintiles. For each point in time (24 h, 72 h, 30 days, and 6 months), the logistic regression model was used in order to determine the relative risk for death and myocardial infarction. The effect of the baseline characteristics and other biochemical markers on any associations between PAPP-A levels and cardiovascular events as observed was performed by using stepwise Cox proportional-hazards regression model. All results of the continuous variables are expressed as median±standard deviation. The comparison between the groups was analysed by a t-test (two-sided). The comparison of categorical variables was generated by the Pearson $\chi^2$ Test. p-values of <0.05 were regarded as statistically significant. All analyses were performed with SPSS 11.5 (SPSS Inc., Chicago).

Summary of the Results

Baseline PAPP-A plasma levels indicated an average level of 14.8±13.8 mIU/l (range 0.2 to 105.4). When the PAPP-A plasma levels were associated with common risk markers, PAPP-A concentrations did not correlate with TnT levels (Spearman row correlation coefficient r=0.11; P=0.16) and were similar in patients with high TnT plasma levels and in patients with low TnT plasma levels (FIG. 14). Similarly, VEGF (r=0.08; P=0.07), and IL-10 plasma levels (r=−0.04; P=35) showed no association with PAPP-A plasma levels. In contrast to this, the hsCRP plasma levels were significantly higher in patients with elevated TnT plasma levels. The bivariant correlation analysis resulted in a significant correlation between PAPP-A and hsCRP as well as between PAPP-A and sCD40L, although the correlation coefficients were low with r=0.21 for hsCRP (P=0.001), and r=0.18 for sCD40L (P=0.001). However, when the analysis was limited to patients without myocardial necrosis (no troponin-increase) the correlation between hsCRP and PAPP-A became more obvious, with an r value of 0.68 (P=0.001). Consequently, patients with elevated PAPP-A levels each exhibited significantly higher hsCRP and sCD40L levels (FIG. 15).

Interaction between PAPP-A Plasma Levels and Cardiac Risk

Patients were stratified in quintiles according to their measured PAPP-A levels: (PAPP-A_1)<4.5 mIU/L (n=111), (PAPP-A_2) 4.5-7.5 mIU/L (n=108), (PAPP-A_3) 7.6-12.6 mIU/l (n=109), (PAPP-A_4) 12.7-24.0 mIU/l (n=110), and (PAPP-A_5)>24.0 mIU/l (n=109), respectively. For the initial 24-hour period, the combined endpoints mortality and non-fatal myocardial infarction did not differ between the quintiles (P=0.69) (FIG. 16). For the 72-hours follow-up, including peri-interventional events, the differences in the cardiac events between the levels that were reached in the quintiles reached statistic significance (P=0.019). During the 30-days and 6-months follow-up, the event-rate-curves continued to diverge from one another leading to highly significant differences between the quintiles both at 30 days (P=0.008), and 6 months follow-up (P=0.004). For the 6-months follow-up data the post hoc analysis of the PAPP-A quintiles using a logistic regression model led to the result that only the upper two PAPP-A quintiles (4. quintile: P=0.034; 5. quintile: P=0.002) differed significantly from the first PAPP-A quintile serving as a reference. In agreement with these results, the receiver-operating characteristics-curve-analysis verified a threshold value of 12.6 mIU/l PAPP-A for the maximised predictive value (FIG. 17).

Stratification According to PAPP-A Status

Figure 18B:
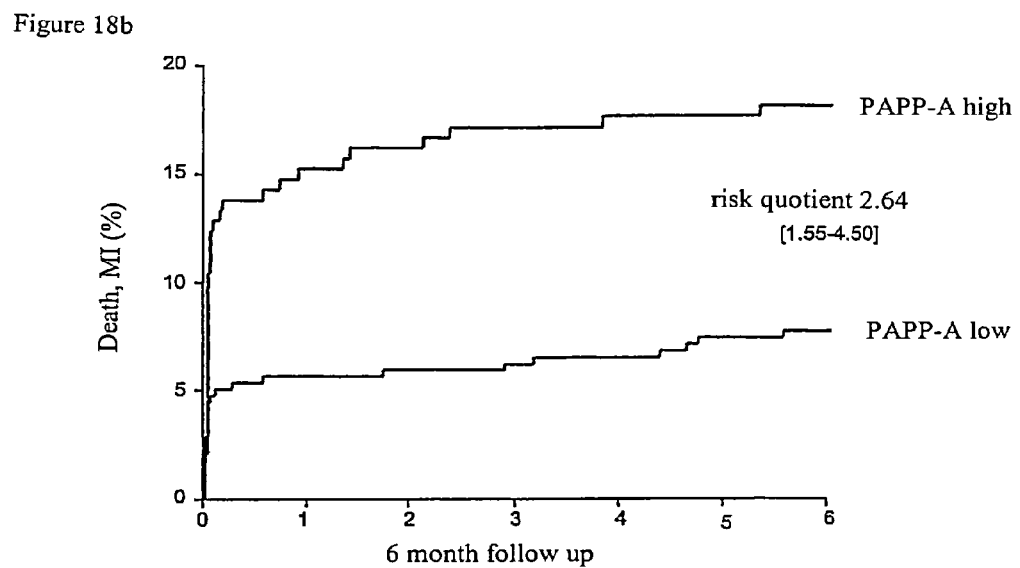

Based on the above mentioned results the study population was dichotomised according to the calculated threshold value of 12.6 mIU/l leading to 219 patients with elevated PAPP-A levels (40.0%). In addition to higher levels of each of hsCRP and sCD40L in patients with elevated PAPP-A plasma levels, the baseline-characteristics in patients with elevated PAPP-A plasma levels were not significantly different from patients with low PAPP-A plasma levels (Table 5). The odds-ratios for death and myocardial infarction (adjusted to differences in den baseline-characteristics) were 1.15 (95% CI 0.36-3.67; P=1.00) at 24 h, 2.96 (95% CI 1.55-5.64; P=0.002) at 72 h (FIG. 18a), 2.84 (95% CI 1.55-5.22; P=0.001) at 30 days, and 2.64 (95% CI 1.55-4.50; P 0.001) at 6 months (FIG. 18b). Six-months cumulative event rates in patients with low PAPP-A levels were 7.9%, versus 17.4% for patients with high PAPP-A levels. These difference in the event rates were not only caused by a higher rate of non-fatal myocardial infarction, but also by a higher mortality in patients with reduced PAPP-A plasma levels (3.2% versus 1.2%; P=0.098). Correspondingly, urgent processes for revascularisation including percutaneous coronary intervention and coronary arterial bypass-grafting were significantly higher in patients with elevated PAPP-A plasma levels (13.6% versus 7.9%; P=0.012). Non-urgent processes for revascularisation during the 6 months of follow-up indicated a higher occurrence in patients with high PAPP-A plasma levels compared to patients with lower PAPP-A plasma levels (34.4% versus 19.7%; P=0.005).

Multimarker-Considerations

Figure 19A:
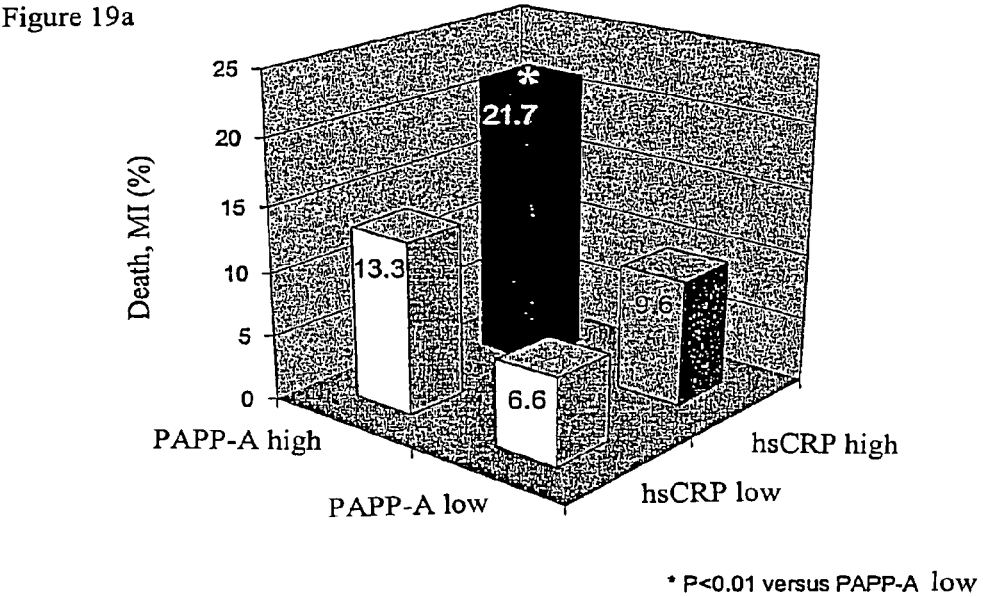
Figure 19B:
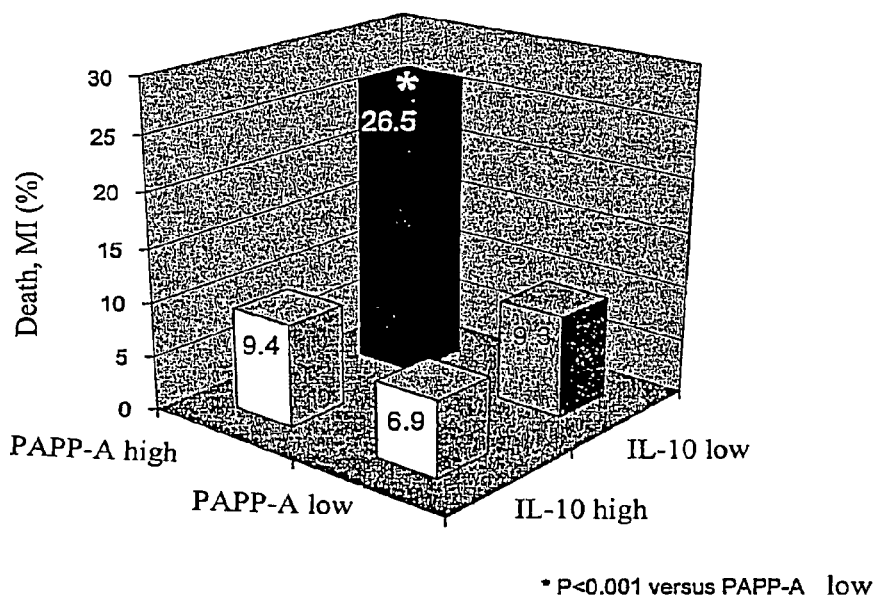
Figure 20A:
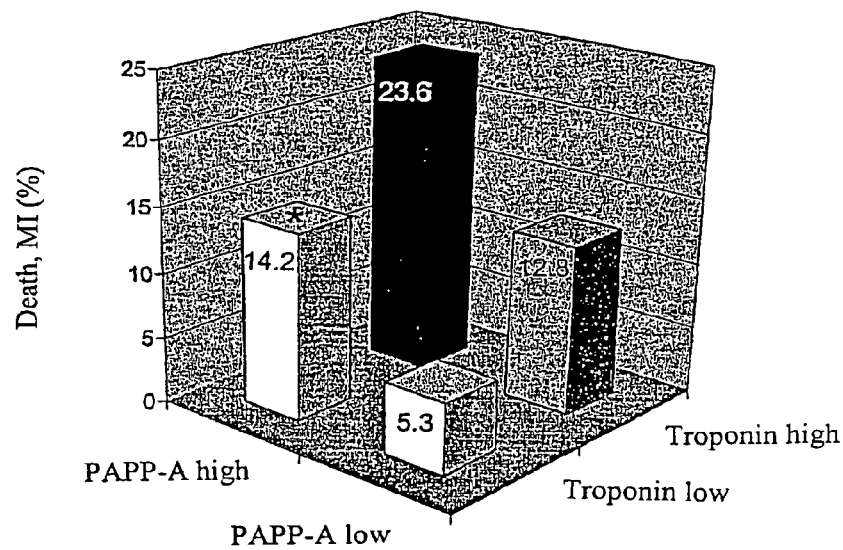
Figure 20B:
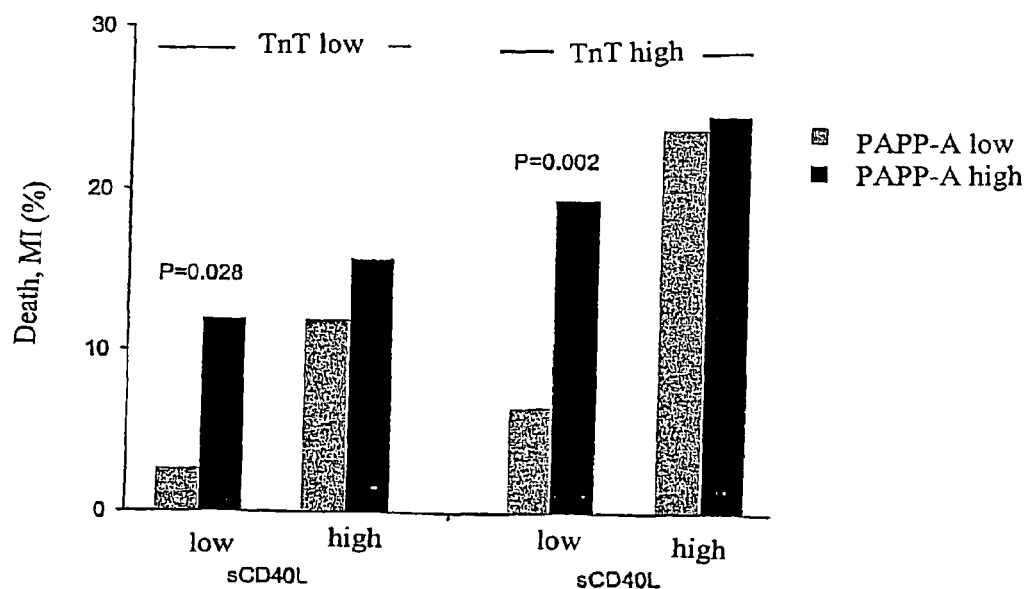

The inventors simultaneously measured markers of myocardial necrosis (TnT), ischemia (VEGF), inflammation (hsCRP, PAPP-A), anti-inflammatory activity (IL-10), and activation of platelets (sCD40L). Remarkably, the predictive value of PAPP-A was limited to patients with elevated hsCRP levels (FIG. 19a). When the hsCRP plasma level was elevated (above 10 mg/l) patients with a PAPP-A plasma level of above the calculated threshold value of 12.6 mIU/l indicated an elevated cardiac risk for death and non-fatal myocardial infarction (adjusted odds-ratio 2.61 [1.25-5.62]; P=0.007) (FIG. 19a). In contrast to this, for patients with hsCRP values below 10 mg/L, PAPP-A did not serve as a significant predictor for the cardiovascular risk (P=0.073). In addition, the predictive value of PAPP-A was tightly associated with the plasma levels of the anti-inflammatory cytokine IL-10 (FIG. 19b). When the IL-10 plasma levels were above the calculated threshold values of 3.5 ng/l, patients with elevated PAPP-A plasma levels (above 12.6 mIU/l) were protected from an elevated cardiac risk (adjusted odds-ratio 1.40 [0.60-3.23]; P<0.001) (FIG. 19b). However, for patients with low IL-10 plasma levels, PAPP-A values above 12.6 mIU/l identified a subgroup of patients that suffered from a particularly high cardiovascular risk (adjusted odds-ratio 3.52 [1.71-7.23]; P 0.001). In summary, these data show that the predictive value of PAPP-A plasma levels is importantly modulated by the balance between pro- and anti-inflammatory cytokine-plasma levels. Importantly, the predictive value of PAPP-A was also visible in patients without evidences for myocardial necrosis. TnT-negative patients (threshold value 0.1 µg/l) with elevated PAPP-A levels were at significantly higher risk compared to TnT-negative patients with low PAPP-A levels (adjusted odds-ratio 2.72 [1.25-5.89]; P=0.009) (FIG. 20a). In contrast to this, TnT-positive patients suffered from an elevated cardiovascular risk being independent from PAPP-A plasma levels. The predictive value of PAPP-A was also observed for a reduced threshold value of 0.01 µg/L for TnT (adjusted odds-ratio 3.97 [1.24-12.68]; P=0.016). In patients that were negative both for TnT and sCD40L, PAPP identified a subgroup that suffered from an elevated cardiovascular risk during 6 months of follow-up (FIG. 20b). In order to further derive a potentially independent prognostic significance of individual biochemical markers a stepwise multivariate logistic regression analysis was performed that included the biochemical markers TnT, VEGF, hsCRP, PAPP-A, IL-10 and sCD40L as well as baseline characteristics that led to a significant predictive value in a univariate model. For the endpoints death and non-fatal myocardial infarction at 30-days and 6-months follow-up, none of the established risk factors was an independent predictor after introducing the dichotomised biochemical markers TnT, hsCRP and sCD40L into the model (Table 6). Thus, the stepwise multivariate analysis was limited to biochemical markers. TnT (P=0.008) and PAPP-A (P=0.007) remained independently significant predictors of the outcome of the patients, whereas hsCRP lost the significance after PAPP-A was introduced into the model (P=0.003 without PAPP-A; P=0.16 after introduction of PAPP-A) (Table 7; step I). PAPP-A remained a significant predictor of the outcome of the patients after the inclusion of the anti-inflammatory cytokine IL-10 (Table 7; step III; P=0.006) and after the inclusion of sCD40L as a marker of the activation of platelets (Table 7; step III; P=0.015). After the inclusion of VEGF as a marker the myocardial ischemia TnT lost its predictive power for the 6-months outcome (Table 7; step IV; P=0.24 after the inclusion of VEGF versus P=0.16 before the inclusion of VEGF), whereas PAPP-A remained a significant independent predictor (P=0.014).

The simultaneous determination of biomarkers with distinct pathophysiological profiles dramatically improves the risk stratification in patients with ACS. Since the PAPP-A, PlGF, and sCD40L levels are relatively stable and no specific sample conditions are required for PAPP-A, PlGF, and sCD40L, these markers appear to be suitable for the routine clinical use. Although inherent limitations for markers remain that are not specific for the coronary arteries and/or the myocardium, PAPP-A, PlGF and sCD40L could represent an important tool for the diagnostic and therapeutic stratification of patients with ACS without evidence for myocardial necrosis.

TABLE 5

Base line characteristics according to the PAPP-A status

|  | PAPP-A low | PAPP-A high | p-value |
|---|---|---|---|
| n | 328 | 219 |  |
| male | 70.2% | 71.9% | 0.62 |
| Age | 60.5 ± 11 | 62.2 ± 10.4 | 0.39 |
| troponin T ≥ 0.1 µg/l | 36.4% | 39.2% | 0.23 |
| VEGF > 300 ng/l | 50.8% | 54.3% | 0.43 |
| CRP ≥ 10.0 µg/l | 37.3% | 56.2% | <0.001 |
| IL-10 < 3.5 ng/l | 57.3% | 53.4% | 0.38 |
| sCD40L > 5.0 µg/l | 33.4% | 51.4% | <0.001 |
| ST-segment depression | 45.1% | 53.6% | 0.062 |
| T-wave inversion | 51.7% | 51.7% | 1.00 |
| History of |  |  |  |
| angina > 4 weeks | 55.5% | 56.3% | 0.64 |
| infarction < 30 days | 13.3% | 12.5% | 0.89 |
| infarction > 30 days | 20.3% | 20.6% | 0.90 |
| PTCA | 17.6% | 17.4% | 0.75 |
| CABG | 3.4% | 3.5% | 0.98 |
| Risk factors |  |  |  |
| Diabetes | 9.5% | 10.7% | 0.97 |
| Hypertension | 34.6% | 37.4% | 0.64 |
| Acute smoker | 40.9% | 42.6% | 0.41 |

TABLE 5-continued

Base line characteristics according to the PAPP-A status

|  | PAPP-A low | PAPP-A high | p-value |
|---|---|---|---|
| Medication before registration |  |  |  |
| Aspirin | 98.1% | 97.8% | 1.00 |
| Heparin i.v. | 99.0% | 98.8% | 1.00 |
| Nitrates i.v. | 99.5% | 99.2% | 1.00 |
| Beta-blockers | 63.5% | 62.9% | 0.94 |

TABLE 6

Multivariate Cox proportional-hazards-regression model for lethal and non-lethal myocardial infarction within the first 6 months of follow-up examination

| Variable | adjusted hazards-ratio | 95% CI | p-value |
|---|---|---|---|
| Gender | 0.91 | 0.68 to 1.39 | 0.16 |
| Age > 65 years | 1.36 | 0.91 to 1.82 | 0.34 |
| Diabetes mellitus | 1.22 | 0.83 to 1.49 | 0.61 |
| Hypercholesterolemia | 0.90 | 0.68 to 1.13 | 0.59 |
| Hypertension | 1.00 | 0.89 to 1.04 | 1.00 |
| History of a coronary-revascularisation | 0.86 | 0.65 to 1.19 | 0.72 |
| ST-depression | 1.29 | 0.72 to 2.31 | 0.39 |
| troponin T > 0.1 µg/l | 2.23 | 1.25 to 3.98 | 0.007 |
| hsCRP > 10.0 mg/l | 2.03 | 1.11 to 3.59 | 0.018 |
| PAPP-A > 12.6 mIU/l | 2.33 | 1.30 to 4.17 | 0.005 |

TABLE 7

Multimarker examinations - stepwise multivariate/logistic regression model for lethal and non-lethal myocardial infarction within the first 6 months of follow-up examination

| Variable | regression-coefficient B | SE | wald | P-value | Exp(B) | 95% CI |
|---|---|---|---|---|---|---|
| step I |  |  |  |  |  |  |
| CRP | 0.38 | 0.28 | 1.82 | 0.16 | 1.49 | 0.86 to 2.59 |
| TnT | 0.72 | 0.27 | 6.88 | 0.008 | 2.07 | 1.21 to 3.56 |
| PAPP-A | 0.83 | 0.27 | 9.01 | 0.007 | 2.13 | 1.24 to 3.68 |
| step II |  |  |  |  |  |  |
| CRP | 0.20 | 0.29 | 0.46 | 0.50 | 1.44 | 0.67 to 2.17 |
| TnT | 0.75 | 0.27 | 7.44 | 0.006 | 2.13 | 1.24 to 3.69 |
| PAPP-A | 0.78 | 0.28 | 7.70 | 0.006 | 2.18 | 1.25 to 3.78 |
| IL-10 | −0.76 | 0.29 | 6.99 | 0.008 | 0.47 | 0.26 to 0.82 |
| step III |  |  |  |  |  |  |
| CRP | 0.20 | 0.30 | 0.47 | 0.49 | 1.23 | 0.68 to 2.19 |
| TnT | 0.66 | 0.28 | 5.51 | 0.019 | 1.93 | 1.12 to 3.35 |
| PAPP-A | 0.70 | 0.29 | 5.60 | 0.015 | 2.05 | 1.18 to 3.32 |
| IL-10 | −0.86 | 0.28 | 9.29 | 0.002 | 0.42 | 0.24 to 0.74 |
| SCD40L | 0.90 | 0.30 | 9.61 | 0.002 | 2.45 | 1.39 to 4.32 |
| step IV |  |  |  |  |  |  |
| TnT | 0.36 | 0.31 | 1.38 | 0.24 | 1.43 | 0.79 to 2.60 |
| PAPP-A | 0.69 | 0.29 | 5.85 | 0.014 | 2.01 | 1.14 to 3.49 |
| IL-10 | −0.84 | 0.28 | 8.66 | 0.003 | 0.43 | 0.25 to 0.76 |
| SCD40L | 0.86 | 0.29 | 8.76 | 0.003 | 2.37 | 1.34 to 4.18 |
| VEGF | 0.78 | 0.33 | 5.63 | 0.018 | 2.29 | 1.14 to 4.18 |

The invention claimed is:

1. A method for diagnosing an acute cardiovascular disease comprising:
(a) obtaining a biological sample from a patient to be analyzed;
(b) measuring a concentration of placental growth factor (PlGF) in the sample;
(c) comparing the results obtained in (b) for the biological sample with a PlGF concentration in at least one reference sample;
(d) using the comparison to diagnose an acute cardiovascular disease.

2. The method of claim 1, wherein the acute cardiovascular disease is chosen from unstable angina, myocardial infarction, acute coronary syndromes, coronary arterial disease, and heart insufficiency.

3. The method of claim 1, further comprising administering a therapy if an acute cardiovascular disease is diagnosed, the therapy comprising administering at least one statin or at least one inhibitor of a glycoprotein IIb/III-receptor.

4. The method of claim 3, wherein the at least one inhibitor of a glycoprotein IIb/III-receptor is abciximab.

5. The method of claim 1, further comprising measuring a concentration of at least one additional marker selected from PAPP-A, soluble CD40-ligand (sCD40L), troponin T (TnT), MPO, NT-proBNP, VEGF, BNP, and IL-10 in the sample.

6. The method of claim 5, wherein a diagnosis of acute cardiovascular disease is indicated by:
(i) a concentration of PlGF above a reference concentration of about 27.0 ng/l and a concentration of PAPP-A above a reference concentration of about 12.6 mIU/l;
(ii) a concentration of PlGF above a reference concentration of about 27.0 ng/l and a concentration of sCD40L above a reference concentration of about 5.0 µg/l;
(iii) a concentration of PlGF above a reference concentration of about 27.0 ng/l and a concentration of TnT above a reference concentration of about 0.1 µg/l;
(iv) a concentration of PlGF above a reference concentration of about 27.0 ng/l and a concentration of VEGF above a reference concentration of about 300 ng/l; or
(v) a concentration of PlGF above a reference concentration of about 27.0 ng/l and a concentration of IL-10 below a reference concentration of about 3.5 ng/l.

7. A method of determining a prognosis for an acute cardiovascular disease comprising:
(a) obtaining a biological sample from a patient to be analyzed;
(b) measuring a concentration of PlGF in the sample;
(c) comparing the results obtained in (b) for the biological sample with a PlGF concentration in at least one reference sample;
(d) using the comparison to determine the prognosis of an acute cardiovascular disease.

8. The method of claim 7, wherein the acute cardiovascular disease is chosen from unstable angina, myocardial infarction, acute coronary syndromes, coronary arterial disease, and heart insufficiency.

9. The method of claim 7, further comprising administering a therapy for an acute cardiovascular disease if a negative prognosis is determined, the therapy comprising administering at least one statin or at least one inhibitor of a glycoprotein IIb/III-receptor.

10. The method of claim 9, wherein the at least one inhibitor of a glycoprotein IIb/III-receptor is abciximab.

11. The method of claim 7, further comprising measuring a concentration of at least one additional marker selected from PAPP-A, soluble CD40-ligand (sCD40L), troponin T (TnT), MPO, NT-proBNP, VEGF, BNP, and IL-10 in the sample.

12. The method of claim 11, wherein a negative prognosis for an acute cardiovascular disease is indicated by:

(i) a concentration of PlGF above a reference concentration of about 27.0 ng/l and a concentration of PAPP-A above a reference concentration of about 12.6 mIU/l;
(ii) a concentration of PlGF above a reference concentration of about 27.0 ng/l and a concentration of sCD40L above a reference concentration of about 5.0 µg/l;
(iii) a concentration of PlGF above a reference concentration of about 27.0 ng/l and a concentration of TnT above a reference concentration of about 0.1 µg/l;
(iv) a concentration of PlGF above a reference concentration of about 27.0 ng/l and a concentration of VEGF above a reference concentration of about 300 ng/l; or
(v) a concentration of PlGF above a reference concentration of about 27.0 ng/l and a concentration of IL-10 below a reference concentration of about 3.5 ng/l.

13. A method of monitoring therapy for an acute cardiovascular disease in a patient, comprising:
(a) obtaining a biological sample from a patient to be analyzed;
(b) measuring a concentration of PlGF in the sample;
(c) comparing the results obtained in (b) for the biological sample with a PlGF concentration in at least one reference sample;
(d) using the comparison to monitor therapy for an acute cardiovascular disease to detect an improvement or lack thereof in a pathophysiological condition; as indicated by a change in the concentration of the PlGF; and
(e) adjusting the therapy for an acute cardiovascular disease, if necessary, in light of the improvement or lack thereof detected in (d).

14. The method of claim 13, wherein the acute cardiovascular disease is chosen from unstable angina, myocardial infarction, acute coronary syndromes, coronary arterial disease, and heart insufficiency.

15. The method of claim 13, wherein the therapy comprises administering at least one statin or at least one inhibitor of a glycoprotein IIb/III-receptor.

16. The method of claim 15, wherein the at least one inhibitor of a glycoprotein IIb/III-receptor is abciximab.

17. The method of claim 13, further comprising measuring a concentration of at least one additional marker selected from PAPP-A, soluble CD40-ligand (sCD40L), troponin T (TnT), MPO, NT-proBNP, VEGF, BNP, and IL-10 in the sample.

18. The method of claim 17, wherein a lack of improvement in a pathophysiological condition is indicated by:
(i) a concentration of PlGF above a reference concentration of about 27.0 ng/l and a concentration of PAPP-A above a reference concentration of about 12.6 mIU/l;
(ii) a concentration of PlGF above a reference concentration of about 27.0 ng/l and a concentration of sCD40L above a reference concentration of about 5.0 µg/l;
(iii) a concentration of PlGF above a reference concentration of about 27.0 ng/l and a concentration of TnT above a reference concentration of about 0.1 µg/l;
(iv) a concentration of PlGF above a reference concentration of about 27.0 ng/l and a concentration of VEGF above a reference concentration of about 300 ng/l; or
(v) a concentration of PlGF above a reference concentration of about 27.0 ng/l and a concentration of IL-10 below a reference concentration of about 3.5 ng/l.

19. A method of treating an acute cardiovascular disease, comprising:
(a) obtaining a biological sample to be analyzed;
(b) measuring a concentration of PlGF or soluble CD40-ligand (sCD40L) in the sample
(c) comparing the results obtained in (b) for the biological sample with a PlGF concentration or a sCD40L concentration in at least one reference sample; and
(d) administering at least one inhibitor of a glycoprotein IIb/III-receptor if the concentration of PlGF measured in (b) is greater than the PlGF concentration in the reference sample in (c), or if the concentration of sCD40L measured in (b) is greater than the sCD40L concentration in the reference sample in (c).

20. The method of claim 19, wherein the at least one inhibitor of a glycoprotein IIb/III-receptor is abciximab.

21. The method of claim 19, wherein the at least one inhibitor of a glycoprotein Milli-receptor is administered if the concentration of PlGF in the biological sample is above a reference concentration of about 27.0 ng/l of if the concentration of sCD40L in the biological sample is above a reference concentration of about 5.0 µg/l.

22. The method of claim 19, wherein the acute cardiovascular disease is chosen from unstable angina, myocardial infarction, acute coronary syndromes, coronary arterial disease, and heart insufficiency.

* * * * *

UNITED STATES PATENT AND TRADEMARK OFFICE
CERTIFICATE OF CORRECTION

PATENT NO. : 8,673,581 B2  
APPLICATION NO. : 13/613010  
DATED : March 18, 2014  
INVENTOR(S) : Andreas M. Zeiher et al.

Page 1 of 1

It is certified that error appears in the above-identified patent and that said Letters Patent is hereby corrected as shown below:

In the Claims:

Claim 6, col. 38, line 30, "about 5.0 μg/I" should read -- about 5.0 μg/l --;

Claim 6, col. 38, line 39, "27.0 ng/ I" should read -- 27.0 ng/l --;

Claim 18, col. 40, line 13, "27.0 ng/I" should read -- 27.0 ng/l --;

Claim 19, col. 40, line 22, insert -- ; -- after "in the sample";

Claim 21, col. 40, line 35, "glycoprotein Milli-receptor" should read -- glycoprotein IIb/III-receptor --;

Claim 21, col. 40, lines 37-38, "of if the concentration" should read -- or if the concentration --.

Signed and Sealed this  
Tenth Day of June, 2014

Michelle K. Lee  
*Deputy Director of the United States Patent and Trademark Office*